US007345143B2

(12) United States Patent
Lassner et al.

(10) Patent No.: US 7,345,143 B2
(45) Date of Patent: Mar. 18, 2008

(54) PLASTID TRANSIT PEPTIDES

(75) Inventors: Michael Lassner, Foster City, CA (US); Jack Q. Wilkinson, Redwood City, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 11/619,318

(22) Filed: Jan. 3, 2007

(65) Prior Publication Data

US 2007/0118925 A1 May 24, 2007

Related U.S. Application Data

(62) Division of application No. 11/449,330, filed on Jun. 8, 2006, which is a division of application No. 11/150, 054, filed on Jun. 9, 2005, now Pat. No. 7,193,133.

(60) Provisional application No. 60/578,535, filed on Jun. 9, 2004.

(51) Int. Cl.
*C07K 5/00* (2006.01)
*C07K 14/00* (2006.01)
*C07H 21/00* (2006.01)

(52) U.S. Cl. ..................... 530/300; 530/370; 536/23.4; 536/23.6

(58) Field of Classification Search ..................... None
See application file for complete search history.

(56) References Cited

U.S. PATENT DOCUMENTS 5,717,084 A 2/1998 Herrera-Estrella et al.

OTHER PUBLICATIONS

Andersson et al., NCBI, GenBank, Sequence Accession No. AJ235272, Published Nov. 11, 1998).*

Benedetti et al., 1998, "Differential Expression of a Novel Gene in Response to Coronatine, Methyl Jasmonate, and Wounding in the Coil Mutant of *Arabidopsis*" Plant Physiol. 116:1037-42.

Bruce, 2000, "Chloroplast Transit Peptides: Structure, Function and Evolution" Trends in Cell Biology 10:440-7.

Bruce, 2001, "The Paradox Of Plastid Transit Peptides: Conservation Of Function Despite Divergence In Primary Structure" Biochimica et Biophysica Acta 1541:2-21.

Claros et al., 1997, "Prediction Of N-Terminal Protein Sorting Signals" Curr. Opin. Struct. Biol. 7(3):394-8.

Davis et al., 1999, "The *Arabidopsis thaliana* HY1 Locus, Required For Phytochrome-Chromophore Biosynthesis, Encodes A Protein Related To Heme Oxygenases" Proc. Natl. Acad. Sci. U.S.A. 96:6541-6.

Davis et al., 2001, "The Heme-Oxygenase Family Required for Phytochrome Chromophore Biosynthesis is Necessary for Proper Photomorphogenesis in Higher Plants" Plant Physiol. 126:656-69.

Emanuelsson et al., 1999, "ChloroP, a Neutral Network-Based Method for Predicting Chloroplast Transit Peptides and Their Cleavage Sites" Protein Science 8:978-84.

Gavel et al., 1990, "A Conserved Cleavage-Site Motif In Chloroplast Transit Peptides" 261(2):455-8.

Tsuchiya et al., 1999, "Cloning of Chlorophyllase, the Key Enzyme in Chlorophyll Degradation: Finding of a Lipase Motif and the Induction by Methyl Jasmonate" Proc. Natl. Acad. Sci. U.S.A. 96:15362-7.

GenBank Accession No. AAD22107, Mar. 2, 1999.

GenBank Accession No. AAK63013, Nov. 8, 2000.

GenBank Accession No. Q9M717, Apr. 1999.

Andersson et al., NCBI, GenBank, Sequence Accession No. AJ235272, pp. 1-133, Published Nov. 11, 1998.

* cited by examiner

*Primary Examiner*—Phuong T. Bui
*Assistant Examiner*—Vinod Kumar
(74) *Attorney, Agent, or Firm*—Morgan & Finnegan, LLP

(57) ABSTRACT

The present invention provides novel plastid transit peptides that direct localization of attached moieties (e.g., polypeptides) into plant plastids. The present invention also relates to methods and compositions for localizing polypeptides to plant plastids including, but not limited to, transgenic plant production.

10 Claims, No Drawings

SEQUENCE LISTING

<160> NUMBER OF SEQ ID NOS: 57

<210> SEQ ID NO 1
<211> LENGTH: 54
<212> TYPE: PRT
<213> ORGANISM: artificial sequence
<220> FEATURE:
<223> OTHER INFORMATION: synthetic peptide -continued

```
<400> SEQUENCE: 1

Met Ala Ala Thr Thr Leu Thr Ser Ala Leu Pro Gly Ala Phe Ser Ser
1               5                   10                  15

Ser Gln Arg Pro Ser Ala Pro Phe Asn Leu Gln Arg Ser Pro Arg Val
            20                  25                  30

Leu Arg Arg Phe Asn Arg Lys Thr Gly Arg Gln Pro Arg Gly Leu Val
        35                  40                  45

Arg Ala Ala Lys Ala Gln
    50


<210> SEQ ID NO 2
<211> LENGTH: 54
<212> TYPE: PRT
<213> ORGANISM: artificial sequence
<220> FEATURE:
<223> OTHER INFORMATION: synthetic peptide

<400> SEQUENCE: 2

Met Ala Ala Thr Ala Val Thr Ser Ala Ser Leu Gly Ala Phe Ser Ser
1               5                   10                  15

Ser Gln Arg Pro Gly Ala Ser Ser Asn Ser Gln Arg Ser Pro Arg Leu
            20                  25                  30

Leu Arg Arg Phe Asn Arg Lys Thr Gly Arg Gln Pro Arg Gly Leu Val
        35                  40                  45

Leu Ala Ala Lys Ala Gln
    50


<210> SEQ ID NO 3
<211> LENGTH: 54
<212> TYPE: PRT
<213> ORGANISM: artificial sequence
<220> FEATURE:
<223> OTHER INFORMATION: synthetic peptide

<400> SEQUENCE: 3

Met Ala Ala Thr Ala Val Ser Ser Val Leu Pro Gly Ala Phe Ser Ser
1               5                   10                  15

Ser Gln Arg Ser Ser Ser Pro Phe Asn Ser Gln Arg Ser Leu Ile Val
            20                  25                  30

Leu Arg Arg Phe Asn Arg Lys Arg Arg Arg Gln Arg Arg Gly Arg Val
        35                  40                  45

Leu Ala Ala Lys Ala Gln
    50


<210> SEQ ID NO 4
<211> LENGTH: 54
<212> TYPE: PRT
<213> ORGANISM: artificial sequence
<220> FEATURE:
<223> OTHER INFORMATION: synthetic peptide

<400> SEQUENCE: 4

Met Ala Ala Thr Thr Val Ser Ser Ala Leu Leu Ser Ala Phe Ser Ser
1               5                   10                  15

Ser Gln Ser Pro Ser Ala Ser Phe Ser Leu Gln Thr Leu Pro Ile Val
            20                  25                  30

Leu Arg Arg Phe Asn Arg Lys Thr Gly Arg Lys Pro Arg Gly Arg Val
        35                  40                  45

Leu Ala Ala Lys Ala Gln
    50
```

-continued

<210> SEQ ID NO 5
<211> LENGTH: 54
<212> TYPE: PRT
<213> ORGANISM: artificial sequence
<220> FEATURE:
<223> OTHER INFORMATION: synthetic peptide

<400> SEQUENCE: 5

```
Met Ala Ala Thr Thr Leu Thr Ser Ala Ser Pro Ser Ala Phe Ser Ser
1               5                   10                  15

Ser Gln Ser Ser Gly Ala Pro Ser Asn Leu Gln Arg Ser Leu Arg Leu
            20                  25                  30

Leu Arg Arg Phe Asn Arg Lys Thr Gly Arg Gln Arg Leu Gly Arg Ile
        35                  40                  45

Arg Ala Ala Lys Ala Gln
    50
```

<210> SEQ ID NO 6
<211> LENGTH: 54
<212> TYPE: PRT
<213> ORGANISM: artificial sequence
<220> FEATURE:
<223> OTHER INFORMATION: synthetic peptide

<400> SEQUENCE: 6

```
Met Ala Ser Ser Ala Leu Ser Ser Ala Ser Pro Gly Ala Phe Ser Ser
1               5                   10                  15

Ser Gln Arg Pro Ser Ala Pro Phe Asn Leu Lys Thr Ser Pro Ile Val
            20                  25                  30

Leu Arg Arg Phe Asn Arg Asn Thr Gly Arg Gln Pro Arg Arg Arg Ile
        35                  40                  45

Arg Ala Ala Lys Ala Gln
    50
```

<210> SEQ ID NO 7
<211> LENGTH: 54
<212> TYPE: PRT
<213> ORGANISM: artificial sequence
<220> FEATURE:
<223> OTHER INFORMATION: synthetic peptide

<400> SEQUENCE: 7

```
Met Ala Ala Ser Ala Leu Ser Ser Ala Ser Leu Ser Ala Phe Ser Ser
1               5                   10                  15

Ser Gln Ser Ser Ser Ala Pro Ser Ser Ser Lys Thr Ser Leu Arg Val
            20                  25                  30

Leu Arg Arg Phe Asn Arg Lys Arg Gly Arg Gln Pro Arg Gly Leu Ile
        35                  40                  45

Arg Ala Ala Lys Ala Gln
    50
```

<210> SEQ ID NO 8
<211> LENGTH: 54
<212> TYPE: PRT
<213> ORGANISM: artificial sequence
<220> FEATURE:
<223> OTHER INFORMATION: synthetic peptide

<400> SEQUENCE: 8

```
Met Ala Ala Thr Ala Val Thr Ser Ala Ser Leu Gly Ala Phe Ser Ser
1               5                   10                  15
```

-continued

```
Ser Gln Ser Pro Ser Ala Pro Ser Ser Ser Lys Lys Ser Leu Arg Val
            20                  25                  30

Leu Arg Arg Phe Asn Arg Lys Thr Gly Arg Lys Pro Arg Gly Arg Val
        35                  40                  45

Arg Ala Ala Lys Ala Gln
    50


<210> SEQ ID NO 9
<211> LENGTH: 54
<212> TYPE: PRT
<213> ORGANISM: artificial sequence
<220> FEATURE:
<223> OTHER INFORMATION: synthetic peptide

<400> SEQUENCE: 9

Met Ala Ser Thr Ala Val Ser Ser Ala Ser Pro Gly Ala Phe Ser Ser
1               5                   10                  15

Ser Gln Ser Ser Gly Ala Pro Ser Asn Leu Gln Arg Ser Pro Ile Leu
            20                  25                  30

Leu Arg Arg Phe Asn Arg Lys Arg Gly Arg Lys Pro Leu Gly Arg Ile
        35                  40                  45

Arg Ala Ala Lys Ala Gln
    50


<210> SEQ ID NO 10
<211> LENGTH: 54
<212> TYPE: PRT
<213> ORGANISM: artificial sequence
<220> FEATURE:
<223> OTHER INFORMATION: synthetic peptide

<400> SEQUENCE: 10

Met Ala Ser Thr Thr Leu Thr Ser Ala Ser Pro Ser Ala Phe Ser Ser
1               5                   10                  15

Ser Gln Arg Pro Ser Ala Pro Ser Asn Ser Gln Arg Ser Pro Arg Val
            20                  25                  30

Leu Arg Arg Phe Asn Arg Lys Arg Gly Arg Lys Pro Leu Arg Arg Val
        35                  40                  45

Leu Ala Ala Lys Ala Gln
    50


<210> SEQ ID NO 11
<211> LENGTH: 54
<212> TYPE: PRT
<213> ORGANISM: artificial sequence
<220> FEATURE:
<223> OTHER INFORMATION: synthetic peptide

<400> SEQUENCE: 11

Met Ala Ala Thr Ala Leu Thr Ser Val Leu Pro Gly Ala Phe Ser Ser
1               5                   10                  15

Ser Gln Ser Pro Ser Ala Pro Phe Ser Leu Gln Arg Ser Pro Ile Val
            20                  25                  30

Leu Arg Arg Phe Asn Arg Asn Arg Gly Arg Gln Pro Arg Gly Arg Val
        35                  40                  45

Arg Ala Ala Lys Ala Gln
    50
```

-continued

<210> SEQ ID NO 12
<211> LENGTH: 54
<212> TYPE: PRT
<213> ORGANISM: artificial sequence
<220> FEATURE:
<223> OTHER INFORMATION: synthetic peptide

<400> SEQUENCE: 12

```
Met Ala Ala Ser Ala Leu Thr Ser Ala Ser Leu Gly Ala Phe Ser Ser
1               5                   10                  15

Ser Gln Arg Pro Ser Ala Pro Ser Asn Leu Gln Thr Ser Pro Ile Val
            20                  25                  30

Leu Arg Arg Phe Asn Arg Lys Thr Gly Leu Gln Pro Arg Arg Arg Val
        35                  40                  45

Arg Ala Ala Lys Ala Gln
    50
```

<210> SEQ ID NO 13
<211> LENGTH: 54
<212> TYPE: PRT
<213> ORGANISM: artificial sequence
<220> FEATURE:
<223> OTHER INFORMATION: synthetic peptide

<400> SEQUENCE: 13

```
Met Ala Ala Thr Ala Leu Thr Ser Ala Ser Pro Ser Ala Phe Ser Ser
1               5                   10                  15

Ser Gln Arg Pro Gly Ala Pro Ser Ser Ser Lys Thr Ser Pro Arg Leu
            20                  25                  30

Leu Arg Arg Phe Asn Arg Asn Thr Arg Arg Gln Arg Arg Gly Leu Val
        35                  40                  45

Arg Ala Ala Lys Ala Gln
    50
```

<210> SEQ ID NO 14
<211> LENGTH: 54
<212> TYPE: PRT
<213> ORGANISM: artificial sequence
<220> FEATURE:
<223> OTHER INFORMATION: synthetic peptide

<400> SEQUENCE: 14

```
Met Ala Ser Thr Ala Val Ser Ser Ala Ser Leu Gly Ala Phe Ser Ser
1               5                   10                  15

Ser Gln Ser Ser Gly Ala Ser Ser Ser Ser Lys Thr Leu Pro Ile Leu
            20                  25                  30

Leu Arg Arg Phe Asn Arg Lys Thr Arg Arg Gln Pro Leu Arg Leu Val
        35                  40                  45

Arg Ala Ala Lys Ala Gln
    50
```

<210> SEQ ID NO 15
<211> LENGTH: 54
<212> TYPE: PRT
<213> ORGANISM: artificial sequence
<220> FEATURE:
<223> OTHER INFORMATION: synthetic peptide

<400> SEQUENCE: 15

```
Met Ala Ala Ser Ala Leu Thr Ser Ala Ser Leu Gly Ala Phe Ser Ser
1               5                   10                  15
```

-continued

```
Ser Gln Ser Pro Gly Ala Pro Ser Ser Ser Gln Thr Ser Leu Arg Val
            20                  25                  30

Leu Arg Arg Phe Asn Arg Lys Thr Gly Pro Gln Arg Leu Arg Arg Val
        35                  40                  45

Arg Ala Ala Lys Ala Gln
    50


<210> SEQ ID NO 16
<211> LENGTH: 54
<212> TYPE: PRT
<213> ORGANISM: artificial sequence
<220> FEATURE:
<223> OTHER INFORMATION: synthetic peptide

<400> SEQUENCE: 16

Met Ala Ser Thr Ala Leu Ser Ser Ala Ser Pro Gly Ala Phe Ser Ser
1               5                   10                  15

Ser Gln Arg Pro Ser Ser Pro Ser Ser Ser Lys Thr Ser Leu Arg Val
            20                  25                  30

Leu Arg Arg Phe Asn Arg Lys Thr Gly Leu Gln Arg Arg Gly Leu Val
        35                  40                  45

Arg Ala Ala Lys Ala Gln
    50


<210> SEQ ID NO 17
<211> LENGTH: 54
<212> TYPE: PRT
<213> ORGANISM: artificial sequence
<220> FEATURE:
<223> OTHER INFORMATION: synthetic peptide

<400> SEQUENCE: 17

Met Ala Ser Ser Ala Leu Ser Ser Ala Ser Pro Gly Ala Phe Ser Ser
1               5                   10                  15

Ser Gln Arg Pro Gly Ser Ser Ser Ser Ser Gln Thr Ser Pro Ile Leu
            20                  25                  30

Leu Arg Arg Phe Asn Arg Lys Thr Gly Arg Gln Arg Leu Arg Arg Val
        35                  40                  45

Arg Ala Ala Lys Ala Gln
    50


<210> SEQ ID NO 18
<211> LENGTH: 54
<212> TYPE: PRT
<213> ORGANISM: artificial sequence
<220> FEATURE:
<223> OTHER INFORMATION: synthetic peptide

<400> SEQUENCE: 18

Met Ala Ala Ser Ala Leu Thr Ser Ala Leu Pro Gly Ala Phe Ser Ser
1               5                   10                  15

Ser Gln Arg Pro Ser Ala Pro Ser Ser Ser Gln Arg Leu Pro Arg Leu
            20                  25                  30

Leu Arg Arg Phe Asn Arg Asn Thr Gly Arg Gln Arg Leu Arg Arg Ile
        35                  40                  45

Arg Ala Ala Lys Ala Gln
    50
```

-continued

```
<210> SEQ ID NO 19
<211> LENGTH: 54
<212> TYPE: PRT
<213> ORGANISM: artificial sequence
<220> FEATURE:
<223> OTHER INFORMATION: synthetic peptide

<400> SEQUENCE: 19

Met Ala Ser Thr Ala Val Thr Ser Val Ser Pro Ser Ala Phe Ser Ser
1               5                   10                  15

Ser Gln Arg Pro Gly Ala Pro Ser Ser Leu Gln Arg Ser Pro Arg Val
            20                  25                  30

Leu Arg Arg Phe Asn Arg Lys Thr Gly Arg Gln Arg Leu Gly Leu Val
        35                  40                  45

Leu Ala Ala Lys Ala Gln
    50


<210> SEQ ID NO 20
<211> LENGTH: 54
<212> TYPE: PRT
<213> ORGANISM: artificial sequence
<220> FEATURE:
<223> OTHER INFORMATION: synthetic peptide

<400> SEQUENCE: 20

Met Ala Ser Thr Ala Val Ser Ser Ala Leu Pro Ser Ala Phe Ser Ser
1               5                   10                  15

Ser Gln Arg Ser Ser Ser Pro Ser Ser Leu Gln Thr Leu Pro Arg Leu
            20                  25                  30

Leu Arg Arg Phe Asn Arg Lys Arg Gly Arg Gln Arg Arg Arg Arg Val
        35                  40                  45

Arg Ala Ala Lys Ala Gln
    50


<210> SEQ ID NO 21
<211> LENGTH: 54
<212> TYPE: PRT
<213> ORGANISM: artificial sequence
<220> FEATURE:
<223> OTHER INFORMATION: synthetic peptide

<400> SEQUENCE: 21

Met Ala Ala Ser Thr Val Ser Ser Val Ser Pro Ser Ala Phe Ser Ser
1               5                   10                  15

Ser Gln Arg Pro Gly Ala Pro Phe Ser Ser Gln Arg Leu Pro Arg Val
            20                  25                  30

Leu Arg Arg Phe Asn Arg Asn Thr Arg Arg Gln Arg Arg Gly Arg Val
        35                  40                  45

Leu Ala Ala Lys Ala Gln
    50


<210> SEQ ID NO 22
<211> LENGTH: 54
<212> TYPE: PRT
<213> ORGANISM: artificial sequence
<220> FEATURE:
<223> OTHER INFORMATION: synthetic peptide

<400> SEQUENCE: 22

Met Ala Ser Thr Ala Leu Thr Ser Ala Leu Leu Gly Ala Phe Ser Ser
1               5                   10                  15
```

-continued

```
Ser Gln Arg Pro Gly Ala Ser Ser Ser Leu Lys Arg Ser Pro Arg Val
            20                  25                  30

Leu Arg Arg Phe Asn Arg Asn Arg Arg Leu Lys Arg Leu Gly Arg Val
        35                  40                  45

Arg Ala Ala Lys Ala Gln
    50


<210> SEQ ID NO 23
<211> LENGTH: 54
<212> TYPE: PRT
<213> ORGANISM: artificial sequence
<220> FEATURE:
<223> OTHER INFORMATION: synthetic peptide

<400> SEQUENCE: 23

Met Ala Ser Thr Thr Val Ser Ser Ala Ser Pro Gly Ala Phe Ser Ser
1               5                   10                  15

Ser Gln Arg Ser Ser Ser Pro Ser Asn Ser Gln Thr Ser Pro Arg Val
            20                  25                  30

Leu Arg Arg Phe Asn Arg Lys Thr Gly Arg Lys Pro Arg Gly Leu Val
        35                  40                  45

Arg Ala Ala Lys Ala Gln
    50


<210> SEQ ID NO 24
<211> LENGTH: 54
<212> TYPE: PRT
<213> ORGANISM: artificial sequence
<220> FEATURE:
<223> OTHER INFORMATION: synthetic peptide

<400> SEQUENCE: 24

Met Ala Ala Thr Ala Val Thr Ser Ala Leu Pro Gly Ala Phe Ser Ser
1               5                   10                  15

Ser Gln Arg Pro Ser Ala Pro Phe Asn Ser Lys Thr Ser Pro Ile Val
            20                  25                  30

Leu Arg Arg Phe Asn Arg Lys Thr Gly Arg Gln Pro Arg Arg Arg Val
        35                  40                  45

Arg Ala Ala Lys Ala Gln
    50


<210> SEQ ID NO 25
<211> LENGTH: 54
<212> TYPE: PRT
<213> ORGANISM: artificial sequence
<220> FEATURE:
<223> OTHER INFORMATION: synthetic peptide

<400> SEQUENCE: 25

Met Ala Ala Ser Thr Leu Ser Ser Val Ser Pro Gly Ala Phe Ser Ser
1               5                   10                  15

Ser Gln Ser Pro Gly Ala Pro Ser Ser Ser Gln Arg Ser Pro Arg Val
            20                  25                  30

Leu Arg Arg Phe Asn Arg Asn Thr Gly Leu Gln Pro Arg Gly Arg Ile
        35                  40                  45

Arg Ala Ala Lys Ala Gln
    50
```

-continued

```
<210> SEQ ID NO 26
<211> LENGTH: 54
<212> TYPE: PRT
<213> ORGANISM: artificial sequence
<220> FEATURE:
<223> OTHER INFORMATION: synthetic peptide

<400> SEQUENCE: 26

Met Ala Ser Ser Ala Leu Thr Ser Ala Ser Pro Gly Ala Phe Ser Ser
1               5                   10                  15

Ser Gln Arg Pro Ser Ala Pro Phe Asn Ser Gln Arg Ser Pro Ile Leu
            20                  25                  30

Leu Arg Arg Phe Asn Arg Asn Thr Arg Arg Gln Arg Arg Gly Leu Ile
        35                  40                  45

Arg Ala Ala Lys Ala Gln
    50


<210> SEQ ID NO 27
<211> LENGTH: 54
<212> TYPE: PRT
<213> ORGANISM: artificial sequence
<220> FEATURE:
<223> OTHER INFORMATION: synthetic peptide

<400> SEQUENCE: 27

Met Ala Ala Ser Ala Leu Thr Ser Val Ser Leu Ser Ala Phe Ser Ser
1               5                   10                  15

Ser Gln Arg Pro Gly Ala Pro Ser Ser Leu Lys Thr Ser Pro Arg Leu
            20                  25                  30

Leu Arg Arg Phe Asn Arg Asn Thr Gly Leu Gln Arg Arg Gly Arg Val
        35                  40                  45

Arg Ala Ala Lys Ala Gln
    50


<210> SEQ ID NO 28
<211> LENGTH: 54
<212> TYPE: PRT
<213> ORGANISM: artificial sequence
<220> FEATURE:
<223> OTHER INFORMATION: synthetic peptide

<400> SEQUENCE: 28

Met Ala Ser Thr Ala Val Ser Ser Ala Leu Leu Ser Ala Phe Ser Ser
1               5                   10                  15

Ser Gln Ser Ser Gly Ser Pro Phe Ser Ser Gln Thr Leu Leu Arg Leu
            20                  25                  30

Leu Arg Arg Phe Asn Arg Asn Thr Gly Arg Gln Pro Leu Arg Arg Val
        35                  40                  45

Leu Ala Ala Lys Ala Gln
    50


<210> SEQ ID NO 29
<211> LENGTH: 54
<212> TYPE: PRT
<213> ORGANISM: artificial sequence
<220> FEATURE:
<223> OTHER INFORMATION: synthetic peptide

<400> SEQUENCE: 29

Met Ala Ala Thr Ala Leu Thr Ser Ala Ser Leu Gly Ala Phe Ser Ser
1               5                   10                  15
```

-continued

Ser Gln Arg Ser Gly Ser Pro Ser Asn Ser Gln Thr Leu Pro Ile Val
20 25 30

Leu Arg Arg Phe Asn Arg Lys Thr Arg Leu Lys Pro Arg Gly Arg Val
35 40 45

Leu Ala Ala Lys Ala Gln
50

<210> SEQ ID NO 30
<211> LENGTH: 54
<212> TYPE: PRT
<213> ORGANISM: artificial sequence
<220> FEATURE:
<223> OTHER INFORMATION: synthetic peptide

<400> SEQUENCE: 30

Met Ala Ser Ser Ala Val Thr Ser Ala Leu Pro Gly Ala Phe Ser Ser
1 5 10 15

Ser Gln Ser Pro Ser Ala Pro Ser Ser Ser Lys Arg Leu Pro Ile Val
20 25 30

Leu Arg Arg Phe Asn Arg Lys Thr Gly Arg Lys Pro Arg Gly Leu Val
35 40 45

Arg Ala Ala Lys Ala Gln
50

<210> SEQ ID NO 31
<211> LENGTH: 54
<212> TYPE: PRT
<213> ORGANISM: artificial sequence
<220> FEATURE:
<223> OTHER INFORMATION: synthetic peptide

<400> SEQUENCE: 31

Met Ala Ala Ser Ala Leu Thr Ser Val Ser Pro Gly Ala Phe Ser Ser
1 5 10 15

Ser Gln Ser Pro Gly Ala Pro Ser Asn Ser Gln Thr Ser Leu Arg Val
20 25 30

Leu Arg Arg Phe Asn Arg Asn Thr Arg Arg Lys Pro Arg Gly Leu Val
35 40 45

Arg Ala Ala Lys Ala Gln
50

<210> SEQ ID NO 32
<211> LENGTH: 54
<212> TYPE: PRT
<213> ORGANISM: artificial sequence
<220> FEATURE:
<223> OTHER INFORMATION: synthetic peptide

<400> SEQUENCE: 32

Met Ala Ala Thr Ala Leu Thr Ser Ala Ser Leu Gly Ala Phe Ser Ser
1 5 10 15

Ser Gln Arg Pro Gly Ser Ser Ser Asn Ser Gln Thr Ser Pro Ile Leu
20 25 30

Leu Arg Arg Phe Asn Arg Lys Thr Arg Leu Gln Arg Arg Arg Arg Val
35 40 45

Arg Ala Ala Lys Ala Gln
50

-continued

<210> SEQ ID NO 33
<211> LENGTH: 54
<212> TYPE: PRT
<213> ORGANISM: artificial sequence
<220> FEATURE:
<223> OTHER INFORMATION: synthetic peptide

<400> SEQUENCE: 33

```
Met Ala Ala Thr Thr Val Thr Ser Ala Ser Leu Gly Ala Phe Ser Ser
1               5                   10                  15

Ser Gln Ser Pro Ser Ala Pro Phe Asn Ser Gln Thr Ser Pro Arg Val
            20                  25                  30

Leu Arg Arg Phe Asn Arg Lys Thr Gly Arg Gln Pro Arg Gly Arg Val
        35                  40                  45

Arg Ala Ala Lys Ala Gln
    50
```

<210> SEQ ID NO 34
<211> LENGTH: 54
<212> TYPE: PRT
<213> ORGANISM: artificial sequence
<220> FEATURE:
<223> OTHER INFORMATION: synthetic peptide

<400> SEQUENCE: 34

```
Met Ala Ser Ser Thr Leu Thr Ser Ala Leu Pro Gly Ala Phe Ser Ser
1               5                   10                  15

Ser Gln Ser Ser Ser Ala Ser Ser Ser Ser Gln Thr Ser Leu Arg Val
            20                  25                  30

Leu Arg Arg Phe Asn Arg Lys Thr Gly Leu Lys Arg Leu Gly Arg Val
        35                  40                  45

Arg Ala Ala Lys Ala Gln
    50
```

<210> SEQ ID NO 35
<211> LENGTH: 54
<212> TYPE: PRT
<213> ORGANISM: artificial sequence
<220> FEATURE:
<223> OTHER INFORMATION: synthetic peptide

<400> SEQUENCE: 35

```
Met Ala Ala Ser Ala Leu Thr Ser Ala Ser Leu Ser Ala Phe Ser Ser
1               5                   10                  15

Ser Gln Ser Ser Gly Ala Ser Ser Ser Ser Gln Arg Ser Leu Arg Val
            20                  25                  30

Leu Arg Arg Phe Asn Arg Lys Thr Gly Arg Gln Arg Arg Arg Arg Val
        35                  40                  45

Leu Ala Ala Lys Ala Gln
    50
```

<210> SEQ ID NO 36
<211> LENGTH: 54
<212> TYPE: PRT
<213> ORGANISM: artificial sequence
<220> FEATURE:
<223> OTHER INFORMATION: synthetic peptide

<400> SEQUENCE: 36

```
Met Ala Ser Thr Thr Val Ser Ser Ala Ser Pro Gly Ala Phe Ser Ser
1               5                   10                  15
```

-continued

```
Ser Gln Arg Pro Gly Ala Ser Ser Ser Leu Gln Arg Ser Pro Arg Val
            20                  25                  30

Leu Arg Arg Phe Asn Arg Asn Arg Gly Arg Gln Arg Arg Gly Arg Val
        35                  40                  45

Leu Ala Ala Lys Ala Gln
    50


<210> SEQ ID NO 37
<211> LENGTH: 54
<212> TYPE: PRT
<213> ORGANISM: artificial sequence
<220> FEATURE:
<223> OTHER INFORMATION: synthetic peptide

<400> SEQUENCE: 37

Met Ala Ser Thr Thr Leu Ser Ser Ala Ser Pro Gly Ala Phe Ser Ser
1               5                   10                  15

Ser Gln Ser Pro Ser Ala Pro Phe Ser Ser Gln Arg Ser Leu Arg Val
            20                  25                  30

Leu Arg Arg Phe Asn Arg Lys Arg Gly Arg Gln Pro Arg Gly Leu Val
        35                  40                  45

Arg Ala Ala Lys Ala Gln
    50


<210> SEQ ID NO 38
<211> LENGTH: 54
<212> TYPE: PRT
<213> ORGANISM: artificial sequence
<220> FEATURE:
<223> OTHER INFORMATION: synthetic peptide

<400> SEQUENCE: 38

Met Ala Ser Thr Thr Leu Ser Ser Ala Ser Leu Gly Ala Phe Ser Ser
1               5                   10                  15

Ser Gln Ser Pro Ser Ala Pro Phe Ser Ser Gln Arg Leu Leu Arg Val
            20                  25                  30

Leu Arg Arg Phe Asn Arg Lys Arg Gly Arg Lys Pro Arg Gly Arg Val
        35                  40                  45

Arg Ala Ala Lys Ala Gln
    50


<210> SEQ ID NO 39
<211> LENGTH: 59
<212> TYPE: PRT
<213> ORGANISM: artificial sequence
<220> FEATURE:
<223> OTHER INFORMATION: synthetic peptide

<400> SEQUENCE: 39

Met Ala Ser Thr Thr Leu Ser Ser Ala Ser Leu Ala Ser Val Ser Leu
1               5                   10                  15

Gly Ala Phe Ser Ser Ser Gln Ser Pro Ser Ala Pro Ser Ser Ser Gln
            20                  25                  30

Thr Ser Pro Ile Val Leu Arg Arg Phe Asn Arg Asn Thr Gly Arg Gln
        35                  40                  45

Pro Arg Arg Leu Val Arg Ala Ala Lys Ala Gln
    50                  55
```

-continued

<210> SEQ ID NO 40
<211> LENGTH: 54
<212> TYPE: PRT
<213> ORGANISM: artificial sequence
<220> FEATURE:
<223> OTHER INFORMATION: synthetic peptide

<400> SEQUENCE: 40

```
Met Ala Ala Ser Thr Leu Ser Ser Ala Ser Pro Ser Ala Phe Ser Ser
1               5                   10                  15

Ser Gln Arg Pro Ser Ala Pro Ser Ser Leu Lys Thr Ser Leu Ile Val
            20                  25                  30

Leu Arg Arg Phe Asn Arg Lys Thr Gly Arg Gln Pro Arg Gly Leu Val
        35                  40                  45

Leu Ala Ala Lys Ala Gln
    50
```

<210> SEQ ID NO 41
<211> LENGTH: 54
<212> TYPE: PRT
<213> ORGANISM: artificial sequence
<220> FEATURE:
<223> OTHER INFORMATION: synthetic peptide

<400> SEQUENCE: 41

```
Met Ala Ala Ser Thr Leu Ser Ser Val Ser Pro Gly Ala Phe Ser Ser
1               5                   10                  15

Ser Gln Arg Ser Gly Ala Pro Ser Asn Leu Gln Arg Ser Pro Ile Leu
            20                  25                  30

Leu Arg Arg Phe Asn Arg Lys Thr Gly Arg Gln Pro Arg Gly Arg Val
        35                  40                  45

Arg Ala Ala Lys Ala Gln
    50
```

<210> SEQ ID NO 42
<211> LENGTH: 54
<212> TYPE: PRT
<213> ORGANISM: artificial sequence
<220> FEATURE:
<223> OTHER INFORMATION: synthetic peptide

<400> SEQUENCE: 42

```
Met Ala Ala Thr Thr Val Ser Ser Ala Leu Pro Gly Ala Phe Ser Ser
1               5                   10                  15

Ser Gln Ser Ser Gly Ser Ser Phe Asn Ser Lys Thr Leu Pro Arg Val
            20                  25                  30

Leu Arg Arg Phe Asn Arg Asn Thr Gly Arg Gln Pro Leu Gly Leu Val
        35                  40                  45

Arg Ala Ala Lys Ala Gln
    50
```

<210> SEQ ID NO 43
<211> LENGTH: 54
<212> TYPE: PRT
<213> ORGANISM: artificial sequence
<220> FEATURE:
<223> OTHER INFORMATION: synthetic peptide

<400> SEQUENCE: 43

```
Met Ala Ser Thr Ala Val Thr Ser Ala Leu Pro Gly Ala Phe Ser Ser
1               5                   10                  15
```

-continued

```
Ser Gln Ser Pro Ser Ala Pro Ser Ser Leu Gln Thr Ser Pro Ile Leu
            20                  25                  30

Leu Arg Arg Phe Asn Arg Asn Arg Gly Leu Lys Arg Leu Gly Arg Ile
        35                  40                  45

Arg Ala Ala Lys Ala Gln
    50


<210> SEQ ID NO 44
<211> LENGTH: 54
<212> TYPE: PRT
<213> ORGANISM: artificial sequence
<220> FEATURE:
<223> OTHER INFORMATION: synthetic peptide

<400> SEQUENCE: 44

Met Ala Ser Ser Ala Leu Thr Ser Ala Ser Pro Ser Ala Phe Ser Ser
1               5                   10                  15

Ser Gln Ser Ser Ser Ala Pro Phe Asn Ser Gln Thr Ser Pro Ile Val
            20                  25                  30

Leu Arg Arg Phe Asn Arg Asn Thr Gly Arg Gln Arg Arg Gly Arg Val
        35                  40                  45

Leu Ala Ala Lys Ala Gln
    50


<210> SEQ ID NO 45
<211> LENGTH: 54
<212> TYPE: PRT
<213> ORGANISM: artificial sequence
<220> FEATURE:
<223> OTHER INFORMATION: synthetic peptide

<400> SEQUENCE: 45

Met Ala Ser Ser Ala Val Thr Ser Ala Ser Pro Ser Ala Phe Ser Ser
1               5                   10                  15

Ser Gln Ser Pro Ser Ala Pro Phe Asn Ser Lys Arg Ser Pro Ile Leu
            20                  25                  30

Leu Arg Arg Phe Asn Arg Lys Thr Gly Leu Gln Pro Arg Arg Leu Val
        35                  40                  45

Arg Ala Ala Lys Ala Gln
    50


<210> SEQ ID NO 46
<211> LENGTH: 54
<212> TYPE: PRT
<213> ORGANISM: artificial sequence
<220> FEATURE:
<223> OTHER INFORMATION: synthetic peptide

<400> SEQUENCE: 46

Met Ala Ala Thr Ala Leu Thr Ser Ala Leu Pro Gly Ala Phe Ser Ser
1               5                   10                  15

Ser Gln Ser Pro Gly Ala Pro Ser Asn Leu Gln Thr Ser Pro Ile Val
            20                  25                  30

Leu Arg Arg Phe Asn Arg Asn Thr Gly Arg Lys Pro Arg Gly Arg Ile
        35                  40                  45

Leu Ala Ala Lys Ala Gln
    50
```

-continued

<210> SEQ ID NO 47
<211> LENGTH: 54
<212> TYPE: PRT
<213> ORGANISM: artificial sequence
<220> FEATURE:
<223> OTHER INFORMATION: synthetic peptide

<400> SEQUENCE: 47

```
Met Ala Ala Thr Thr Leu Ser Ser Ala Leu Pro Gly Ala Phe Ser Ser
1               5                   10                  15

Ser Gln Ser Ser Ser Ala Pro Ser Asn Ser Gln Thr Ser Pro Ile Leu
            20                  25                  30

Leu Arg Arg Phe Asn Arg Lys Thr Gly Leu Gln Pro Arg Arg Arg Val
        35                  40                  45

Leu Ala Ala Lys Ala Gln
    50
```

<210> SEQ ID NO 48
<211> LENGTH: 54
<212> TYPE: PRT
<213> ORGANISM: artificial sequence
<220> FEATURE:
<223> OTHER INFORMATION: synthetic peptide

<400> SEQUENCE: 48

```
Met Ala Ala Thr Ala Leu Ser Ser Ala Ser Leu Gly Ala Phe Ser Ser
1               5                   10                  15

Ser Gln Arg Pro Gly Ala Ser Ser Ser Leu Gln Arg Ser Leu Ile Val
            20                  25                  30

Leu Arg Arg Phe Asn Arg Lys Thr Gly Arg Gln Arg Arg Gly Arg Val
        35                  40                  45

Leu Ala Ala Lys Ala Gln
    50
```

<210> SEQ ID NO 49
<211> LENGTH: 54
<212> TYPE: PRT
<213> ORGANISM: artificial sequence
<220> FEATURE:
<223> OTHER INFORMATION: synthetic peptide

<400> SEQUENCE: 49

```
Met Ala Ser Ser Ala Val Thr Ser Ala Ser Leu Ser Ala Phe Ser Ser
1               5                   10                  15

Ser Gln Arg Pro Ser Ala Ser Phe Asn Leu Gln Thr Ser Pro Arg Val
            20                  25                  30

Leu Arg Arg Phe Asn Arg Lys Thr Gly Arg Gln Arg Leu Gly Leu Val
        35                  40                  45

Arg Ala Ala Lys Ala Gln
    50
```

<210> SEQ ID NO 50
<211> LENGTH: 54
<212> TYPE: PRT
<213> ORGANISM: artificial sequence
<220> FEATURE:
<223> OTHER INFORMATION: synthetic peptide

<400> SEQUENCE: 50

```
Met Ala Ala Thr Ala Leu Thr Ser Ala Leu Leu Gly Ala Phe Ser Ser
1               5                   10                  15
```

-continued

```
Ser Gln Ser Pro Gly Ala Ser Ser Ser Leu Gln Thr Ser Leu Ile Val
            20                  25                  30

Leu Arg Arg Phe Asn Arg Asn Arg Gly Arg Gln Pro Arg Gly Arg Ile
        35                  40                  45

Leu Ala Ala Lys Ala Gln
    50


<210> SEQ ID NO 51
<211> LENGTH: 54
<212> TYPE: PRT
<213> ORGANISM: artificial sequence
<220> FEATURE:
<223> OTHER INFORMATION: synthetic peptide

<400> SEQUENCE: 51

Met Ala Ala Ser Thr Leu Ser Ser Val Ser Pro Gly Ala Phe Ser Ser
1               5                   10                  15

Ser Gln Ser Pro Gly Ala Pro Ser Ser Ser Gln Arg Ser Pro Arg Val
            20                  25                  30

Leu Arg Arg Phe Asn Arg Asn Thr Gly Leu Gln Pro Arg Gly Arg Ile
        35                  40                  45

Arg Ala Ala Lys Ala Gln
    50


<210> SEQ ID NO 52
<211> LENGTH: 51
<212> TYPE: PRT
<213> ORGANISM: artificial sequence
<220> FEATURE:
<223> OTHER INFORMATION: synthetic peptide

<400> SEQUENCE: 52

Met Ala Ala Ser Ala Val Ser Pro Gly Ala Phe Ser Ser Ser Gln Ser
1               5                   10                  15

Pro Gly Ala Ser Ser Asn Ser Gln Arg Leu Leu Arg Val Leu Arg Arg
            20                  25                  30

Phe Asn Arg Lys Thr Gly Leu Gln Pro Leu Gly Arg Ile Arg Ala Ala
        35                  40                  45

Lys Ala Gln
    50


<210> SEQ ID NO 53
<211> LENGTH: 54
<212> TYPE: PRT
<213> ORGANISM: artificial sequence
<220> FEATURE:
<223> OTHER INFORMATION: synthetic peptide

<400> SEQUENCE: 53

Met Ala Ala Thr Ala Leu Ser Ser Ala Ser Pro Gly Ala Phe Ser Ser
1               5                   10                  15

Ser Gln Arg Pro Ser Ala Pro Ser Asn Ser Gln Thr Leu Pro Arg Val
            20                  25                  30

Leu Arg Arg Phe Asn Arg Asn Thr Arg Arg Gln Pro Arg Gly Leu Val
        35                  40                  45

Leu Ala Ala Lys Ala Gln
    50
```

-continued

```
<210> SEQ ID NO 54
<211> LENGTH: 54
<212> TYPE: PRT
<213> ORGANISM: artificial sequence
<220> FEATURE:
<223> OTHER INFORMATION: synthetic peptide

<400> SEQUENCE: 54

Met Ala Ala Thr Ala Val Ser Ser Ala Ser Pro Gly Ala Phe Ser Ser
1               5                   10                  15

Ser Gln Arg Ser Ser Ala Pro Ser Ser Ser Gln Arg Leu Pro Ile Val
            20                  25                  30

Leu Arg Arg Phe Asn Arg Lys Arg Gly Arg Gln Arg Arg Gly Leu Val
        35                  40                  45

Leu Ala Ala Lys Ala Gln
    50


<210> SEQ ID NO 55
<211> LENGTH: 54
<212> TYPE: PRT
<213> ORGANISM: artificial sequence
<220> FEATURE:
<223> OTHER INFORMATION: synthetic peptide

<400> SEQUENCE: 55

Met Ala Ala Ser Ala Leu Thr Ser Val Leu Pro Gly Ala Phe Ser Ser
1               5                   10                  15

Ser Gln Arg Pro Ser Ala Pro Ser Asn Ser Lys Arg Leu Pro Arg Leu
            20                  25                  30

Leu Arg Arg Phe Asn Arg Asn Thr Gly Leu Gln Pro Arg Gly Arg Ile
        35                  40                  45

Leu Ala Ala Lys Ala Gln
    50


<210> SEQ ID NO 56
<211> LENGTH: 54
<212> TYPE: PRT
<213> ORGANISM: artificial sequence
<220> FEATURE:
<223> OTHER INFORMATION: synthetic peptide

<400> SEQUENCE: 56

Met Ala Ser Ser Ala Leu Ser Ser Ala Ser Leu Gly Ala Phe Ser Ser
1               5                   10                  15

Ser Gln Ser Pro Ser Ala Ser Phe Ser Ser Gln Thr Ser Pro Arg Leu
            20                  25                  30

Leu Arg Arg Phe Asn Arg Lys Thr Gly Leu Lys Arg Leu Gly Arg Val
        35                  40                  45

Arg Ala Ala Lys Ala Gln
    50


<210> SEQ ID NO 57
<211> LENGTH: 54
<212> TYPE: PRT
<213> ORGANISM: artificial sequence
<220> FEATURE:
<223> OTHER INFORMATION: synthetic peptide

<400> SEQUENCE: 57

Met Ala Ala Thr Thr Leu Ser Ser Ala Leu Pro Gly Ala Phe Ser Ser
1               5                   10                  15
```

-continued

```
Ser Gln Ser Ser Ser Ala Pro Ser Asn Ser Gln Thr Ser Pro Ile Leu
            20                  25                  30

Leu Arg Arg Phe Asn Arg Lys Thr Gly Leu Gln Pro Arg Arg Arg Val
        35                  40                  45

Leu Ala Ala Lys Ala Gln
    50
```

PLASTID TRANSIT PEPTIDES

This application is a divisional of co-pending application Ser. No. 11/449,330, filed Jun. 8, 2006, which is a divisional of U.S. application Ser. No. 11/150,054 filed Jun. 9, 2005, now U.S. Pat. No. 7,193,133, which claims priority to and benefit of U.S. provisional application No. 60/578,535, filed Jun. 9, 2004, each of which is incorporated herein by reference in their entireties.

1. FIELD OF THE INVENTION

The present invention relates generally to the field of protein targeting and provides peptides that direct localization of attached polypeptides into plant plastids. The present invention also relates to methods and compositions for localizing polypeptides to plant plastids including, but not limited to, transgenic plant production.

2. BACKGROUND OF THE INVENTION

Plastid transit peptides are N-terminal extensions that facilitate the targeting and translocation of cytosolically synthesized precursor proteins into plastids via a post-translational mechanism (reviewed by Bruce, *Biochim. Biophys. Acta* 1541:2-21 (2001)). With the sequencing of the entire *Arabidopsis* genome now completed, it is estimated that more than 3500 different proteins are targeted into the plastids during the life of a typical plant. Developing a model for how all of these targeting sequences function to direct proper targeting has been difficult, since they are highly divergent at the primary sequence level in terms of length, composition, and organization. Secondary and tertiary structural information is only available for a few plastid transit peptides, and the results differ significantly depending on whether the experiments were carried out in an aqueous or membrane-mimetic environment. Thus, no common structural features or properties have been clearly delineated.

The capability to target recombinant proteins to different subcellular compartments in transgenic plants is an important part of plant genetic engineering. For example, many important plant physiological processes take place in plastids including, but not limited to, photosynthesis, fatty acid synthesis, amino acid synthesis, carotenoid biosynthesis, terpenoid biosynthesis, and starch biosynthesis. As such, there is a need for the ability to target recombinant polypeptides to plastids to modulate or alter the physiological processes that occur in the plastids. Additionally, some polypeptides are toxic when expressed recombinantly in the cytoplasm. Because plastids are subcellular compartments, it is possible to target recombinant polypeptides to the plastids to sequester them from the cytoplasm, thus allowing for higher expression levels. Furthermore, expression of recombinant polypeptides in plastids may facilitate isolation of the polypeptide for various applications.

3. SUMMARY OF THE INVENTION

The present invention relates to a novel plastid transit peptides selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:1, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57. In addition to the polypeptide sequences of SEQ ID NOS:1-57, it will be appreciated that peptides of the invention also encompass variants thereof, including, but not limited to, any fragment, derivative, or analog thereof.

The present invention also relates to nucleic acid molecules that encode any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57, or any variants (e.g., any fragment, derivative, or analog) thereof. Nucleic acid molecules that encode peptides with plastid transit functional activity (e.g., the ability to direct an attached moiety into a plastid) and hybridize under stringent conditions to any of the nucleic acid molecules that encode any of SEQ ID NOS:1-57 are also encompassed.

Vectors or expression cassettes comprising nucleic acid molecules of the invention are also encompassed. Cells, plants, or seeds comprising the vectors of the invention are also encompassed.

The present invention also relates to transgenic plants expressing a nucleic acid molecule and/or peptide of the invention. The transgenic plants can express the transgene in any way known in the art including, but not limited to, constitutive expression, developmentally regulated expression, tissue specific expression, etc. Seeds obtained from a transgenic plant of the invention are also encompassed.

Methods of production of the peptides of the invention and/or polypeptides comprising one or more peptides of the invention, e.g., by recombinant means, are also provided. Compositions comprising one or more peptides of the invention and/or polypeptides comprising one or more peptides of the invention are also encompassed.

The present invention also provides methods for targeting a polypeptide to a plastid in a plant by attaching a plastid transit peptide of the invention to the polypeptide to be targeted. In some embodiments, the method comprises recombinantly attaching a first nucleic acid molecule encoding a plastid transit peptide of the invention to a second nucleic acid molecule encoding a polypeptide to be targeted such that translation of the nucleic acid molecule produces a fusion polypeptide.

Methods of identifying novel plastid transit peptides are encompassed by the present invention comprising i) introducing into a plant or plant cell a vector comprising a first nucleic acid molecule encoding a candidate plastid transit peptide linked to a second nucleic acid molecule encoding a polypeptide that is only active in a plastid such that translation of the first and second nucleic acid molecule produces a fusion protein and ii) screening for activity of the polypeptide, wherein said activity indicates that the polypeptide is localized to a plastid and the candidate plastid transit peptide is functional.

3.1 Definitions

A "plastid transit peptide" refers to an amino acid sequence that mediates targeting or localization of an amino acid sequence to which it is attached (e.g., as a fusion polypeptide) to a plastid.

A "plastid" refers to a small, double-membraned organelle of plant cells and certain protists that contains ribosomes, DNA, and, often, pigment. Plastids can occur in an undifferentiated form (proplastid) and several differentiated forms including, but not limited to chloroplasts, etioplasts, amyloplasts, chromoplasts, elaioplasts, and leucoplasts.

The terms "nucleic acid molecule" or "polynucleotide" refer to deoxyribonucleotides or ribonucleotides and polymers thereof in either single- or double-stranded form. Unless specifically limited, the term encompasses nucleic acid molecules containing known analogues of naturally occurring nucleotides that have similar binding properties as the reference nucleotides and are metabolized in a manner similar to naturally occurring nucleotides.

The terms "polypeptide," "peptide" and "protein" refer to a polymer of amino acid residues. The terms apply to amino acid polymers containing naturally occurring amino acid residues as well as amino acid polymers in which one or more amino acid residues is an artificial chemical mimetic of a corresponding naturally occurring amino acid (e.g., non-classical amino acid). The amino acid residues of amino acid polymers are generally linked by covalent peptide bonds but may be linked by any other method known in the art. As used herein, the terms encompass amino acid polymers of any length, including full-length proteins.

The term "amino acid" refers to naturally occurring amino acids, synthetic amino acids, as well as amino acid analogs and mimetics that function in a manner similar to the naturally occurring amino acids. Naturally occurring amino acids are those encoded by the genetic code. Amino acid analogs include, but are not limited to naturally occurring amino acids that are later modified, e.g., hydroxyproline, γ-carboxyglutamate, and O-phosphoserine. Amino acids may be referred to herein by either the commonly known three letter symbols or by the one-letter symbols recommended by the IUPAC-IUB Biochemical Nomenclature Commission.

The term "promoter" refers to regions or sequence located upstream and/or downstream from the start of transcription that are involved in recognition and binding of RNA polymerase and other proteins to initiate transcription. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "vector" refers to a nucleic acid molecule capable of replication in a host cell independently of and/or integrated into the host chromosome. Vectors may be, e.g., plasmids and may have an origin of replication and/or expression elements such as transcription/translation initiators and terminators and promoters useful for regulation of the expression of the particular nucleic acid molecule.

An "expression cassette" refers to a nucleic acid molecule which, when introduced into a host cell, results in transcription of a RNA transcript corresponding to at least a portion of the expression cassette and translation of a peptide or polypeptide from the RNA transcript. The nucleic acid molecule may contain a transcriptional start and/or stop codon.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "Bt toxin" refers to an insecticidal protein isolated or derived from *Bacillus thuringiensis* (Bt) bacteria. The term includes naturally and non-naturally occurring variants, including fragments and modified versions of naturally-occurring Bt toxins. (See, e.g., U.S. Pat. Nos. 6,489,542; 5,281,530; 5,322,932; U.S. patent application Ser. No. 11/067,557 filed Feb. 25, 2005; and PCT publication WO 92/04453.)

The term "recombinant" refers to a human-manipulated polynucleotide, a copy, or complement thereof. For instance, a recombinant expression cassette comprising a promoter operably linked to a second polynucleotide may include a promoter that may be heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

The term "variant polypeptide" refers to a polypeptide that is related to any one of SEQ ID NO:1-57 but has been altered in some respect (e.g., deletion/addition of one or more residues, or making a derivative or analog polypeptide). In some embodiments variant polypeptides have at least partial plastid transit functional activity (e.g., the ability to direct an attached moiety into a plastid) of at least 50%, 60%, 70%, 75%, 85%, 90%, 95%, 97%, 98%, or 99% when compared to the unaltered polypeptide. In other embodiments, variant polypeptides have the same or better plastid transit functional activity when compared to the unaltered polypeptide. Generally, variant polypeptides are created in order to accentuate a desirable characteristic (e.g., increase targeting efficiency, impart plastid specificity, make transcription and/or translation more efficient) or reduce an undesirable characteristic (e.g., degradation susceptibility) of a plastid transit peptide or a polypeptide comprising a plastid transit peptide. Variant polypeptides do not encompass any naturally occurring plastid transit peptides.

A variety of diversity generating protocols are available and described in the art. See, e.g., Ling et al. (1997) *Anal Biochem.* 254(2): 157-178; Dale et al. (1996) *Methods Mol. Biol.* 57:369-374; U.S. Pat. Nos. 5,605,793, 5,811,238, 5,830,721, 5,834,252, 5,837,458, WO 95/22625, WO 96/33207, WO 97/20078, WO 97/35966, WO 99/41402, WO 99/41383, WO 99/41369, EP 752008, EP 0932670, WO 99/23107, WO 99/21979, WO 98/31837, WO 98/27230, WO 98/13487, WO 00/09679, WO 98/42832, WO 99/29902, WO 98/41653, WO 98/41622, WO 00/42561, WO 00/42560, WO 01/75767 and WO 98/42727.

The term "derivative polypeptide" refers to a polypeptide that is related to any one of SEQ ID NOS:1-57 but has been altered by one or more amino acid residue changes yet retains at least partial plastid transit functional activity. In some embodiments, the amino acid residue substituted is a chemically similar amino acid. Conservative substitution tables providing functionally similar amino acids are well known in the art (see, e.g., Creighton, *Proteins* (1984)). For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). In other embodiments, the amino acid residue substituted is not a conservative substitution. Derivative polypeptides may have less than 30%, 25%, 20%, 15%, 10%, 5%, 3%, 1% of their residues altered when compared to the unaltered polypeptide.

Sequence alterations can be introduced by standard techniques such as directed molecular evolution techniques e.g., DNA shuffling methods (see e.g., Christians et al., 1999, *Nature Biotechnology* 17:259-264; Crameri et al, 1998, *Nature,* 391:288-291; Crameri, et al, 1997, *Nature Biotechnology* 15:436-438; Crameri et al., 1996, *Nature Biotechnology* 14:315-319; Stemmer, 1994, *Nature* 370:389-391; Stemmer et al., 1994, *Proc. Natl. Acad. Sci.,* 91:10747-10751; U.S. Pat. Nos. 5,605,793; 6,117,679; 6,132,970; 5,939,250; 5,965,408; 6,171,820; International Publication Nos. WO 95/22625; WO 97/0078; WO 97/35966; WO 98/27230; WO 00/42651; and WO 01/75767); site-directed mutagenesis (see e.g., Kunkel, 1985, *Proc. Natl. Acad. Sci.,* 82:488-492; Oliphant et al, 1986, *Gene* 44:177-183); oligonucleotide-directed mutagenesis (see e.g., Reidhaar-Olson et al., 1988, *Science* 241:53-57); chemical mutagenesis (see e.g., Eckert et al., 1987, *Mutat. Res.* 178:1-10); error-prone PCR (see e.g., Caldwell & Joyce, 1992, *PCR Methods Applic.* 2:28-33); and cassette mutagenesis (see e.g., Arkin et al., *Proc. Natl. Acad. Sci.,* 1992, 89:7871-7815); (see generally, e.g., Arnold, 1993, *Curr. Opinion Biotechnol.* 4:450-455; Ling et al., 1997, *Anal. Biochem.,* 254(2):157-78; Dale et al., 1996, *Methods Mol. Biol.* 57:369-74; Smith, 1985, *Ann. Rev. Genet.* 19:423-462; Botstein et al., 1985, *Science,* 229:1193-1201; Carter, 1986, *Biochem. J.* 237:1-7; Kramer et al., 1984, *Cell* 38:879-887; Wells et al., 1985, *Gene* 34:315-323; Minshull et al, 1999, *Current Opinion in Chemical Biology* 3:284-290).

Additionally, the nucleic acid molecules that encode derivative polypeptides can be codon-optimized, either wholly or in part. Because any one amino acid (except for methionine) is encoded by a number of codons, the sequence of the nucleic acid molecule may be changed without changing the encoded amino acid. Codon optimization is when one or more codons are altered at the nucleic acid level to coincide with or better approximate the codon usage of a particular host. The frequency of preferred codon usage exhibited by a host cell can be calculated by averaging frequency of preferred codon usage in a large number of genes expressed by the host cell. This analysis may be limited to genes that are highly expressed by the host cell. U.S. Pat. No. 5,824,864, for example, provides the frequency of codon usage by highly expressed genes exhibited by dicotyledonous plants and monocotyledonous plants. Those having ordinary skill in the art will recognize that tables and other references providing preference information for a wide range of organisms are available in the art.

The term "analog polypeptide" refers to polypeptides that possess residues that have been modified, i.e., by the covalent attachment of any type of molecule. For example, but not by way of limitation, an analog polypeptide may be modified, e.g., by glycosylation, acetylation, pegylation, phosphorylation, amidation, derivatization by known protecting/blocking groups, proteolytic cleavage, linkage to a cellular ligand or other protein, etc. An analog polypeptide may be modified by chemical modifications using techniques known to those of skill in the art, including, but not limited to specific chemical cleavage, acetylation, formylation, metabolic synthesis of tunicamycin, etc. Furthermore, an analog of a polypeptide may contain one or more non-classical amino acids.

The term "identical" in connection to nucleic acid molecules and polypeptides refers to two sequences that have identical residues when aligned for maximum correspondence as described below.

The term "percent identity" in connection to nucleic acid molecules and polypeptides refers to the percent of residues in two sequences that are identical when compared and aligned for maximum correspondence over a comparison window, as measured using one of the following sequence comparison algorithms or by manual alignment and visual inspection.

When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic.*

*Biol. Sci.* 4:11-17 (1988) e.g., as implemented in the program PC/GENE (Intelligenetics, Mountain View, Calif., USA).

When percentage of sequence identity is used in reference to nucleic acid molecules, any method known in the art can be used. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments, or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "stringent conditions" in connection to nucleic acid hybridization refers to hybridization conditions under which a nucleic acid molecule will hybridize to its target nucleic acid molecule, typically in a complex mixture of nucleic acid molecules, but to essentially no other nucleic acids. Stringent conditions are sequence-dependent and will be different in different circumstances. Longer nucleic acids hybridize specifically at higher temperatures. Extensive guides to the hybridization of nucleic acids can be found in the art (e.g., Tijssen, *Techniques in Biochemistry and Molecular Biology—Hybridization with Nucleic Probes*, "Overview of principles of hybridization and the strategy of nucleic acid assays" (1993)). Generally, highly stringent conditions are selected to be about 5-10° C. lower than the thermal melting point ($T_m$) for the specific nucleic acid at a defined ionic strength pH. Low stringency conditions are generally selected to be about 15-30° C. below the $T_m$. The $T_m$ is the temperature (under defined ionic strength, pH, and nucleic acid concentration) at which 50% of the probes complementary to the target hybridize to the target nucleic acid at equilibrium (as the target nucleic acids are present in excess, at $T_m$, 50% of the probes are occupied at equilibrium). Hybridization conditions are typically those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, and preferably 10 times background hybridization. In one embodiment, stringent conditions include at least one wash (usually 2) in 0.2×SSC at a temperature of at least about 50° C., usually about 55° C., or sometimes 60° C. or 65° C., for 20 minutes, or substantially equivalent conditions. In a specific embodiment, a nucleic acid molecule of the invention specifically hybridizes following at least one wash in 0.2×SSC at 55° C. for 20 minutes to a nucleic acid molecule encoding any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57. In another embodiment, stringent conditions include hybridization in 6× sodium chloride/sodium citrate (SSC) at about 45° C. followed by one or more washes in 0.2×SSC, 0.1% SDS at 50-65° C.

The phrase "specifically hybridizes" refers to the binding, duplexing, or hybridizing of a molecule only to a particular nucleotide sequence under stringent hybridization conditions when that sequence is present in a complex mixture (e.g., total cellular or library DNA or RNA).

The term "substantially similar" when used in connection with plastid transit peptide functional activity refers to two plastid transit peptides having a level of activity that is similar to each other. In some embodiments, plastid transit peptides have substantially similar activity when their activities, as measured in an assay, are one standard deviation or less away from each other. In other embodiments, plastid transit peptides have substantially similar activity when one of the peptide's activity is at least 75%, 80%, 85%, 90%, 95%, 99% of the activity of the other peptide as measured in the same assay.

4. DETAILED DESCRIPTION OF THE INVENTION

The present invention provides novel plastid transit peptides. Nucleic acid molecules encoding the polypeptides of the invention are also provided. Methods for using the peptides and nucleic acid molecules of the invention to target polypeptides to plant plastids (e.g., chloroplasts, etioplasts, amyloplasts, chromoplasts, elaioplasts, and leucoplasts) are encompassed.

4.1 Polypeptides of the Invention

The present invention relates to a novel plastid transit peptides selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57. In addition to the polypeptide sequences of SEQ ID NOS:1-57, it will be appreciated that peptides of the invention also encompass variants thereof, including, but not limited to, any fragment, derivative, or analog thereof. In preferred embodiments, the variant plastid transit peptides have substantially similar or improved activity when compared to non-variant plastid transit peptides.

In one embodiment, peptides encompassed by the present invention have plastid transit functional activity (e.g., the ability to direct an attached moiety into a plastid) and are at least 85%, 90%, 95%, 97%, 98%, or 99% identical to the peptide sequence of any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:1, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57.

In another embodiment, peptides encompassed by the present invention have plastid transit functional activity (e.g., the ability to direct an attached moiety into a plastid) and are a fragment comprising at least 70%, 75%, 85%, 90%, 95%, 97%, 98%, or 99% of the contiguous amino acid residues of any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57.

In another embodiment, peptides encompassed by the present invention have plastid transit functional activity (e.g., the ability to direct an attached moiety into a plastid) and are encoded by a nucleic acid molecule comprising a nucleotide sequence that is at least 95% identical to any of the nucleic acid molecules that encode any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57.

Methods of production of the peptides of the invention and/or polypeptides that comprise peptides of the invention, e.g., by recombinant means, are provided (see Section 4.6).

Compositions comprising one or more peptides of the invention and/or polypeptides that comprise peptides of the invention are also encompassed. The compositions of the invention can further comprise additional agents including, but not limited to, spreader-sticker adjuvants, stabilizing agents, diluents, agents that optimize the rheological properties or stability of the composition, such as, for example, surfactants, emulsifiers, dispersants, and/or polymers.

4.2 Fusion Polypeptides

The present invention provides methods for targeting a polypeptide to a plant plastid by attaching a plastid transit peptide of the invention to the polypeptide to be targeted. In preferred embodiments, the method comprises recombinantly attaching a first nucleic acid molecule encoding a plastid transit peptide of the invention to a second nucleic acid molecule encoding a polypeptide to be targeted such that translation of the nucleic acid molecule produces a fusion polypeptide. The fusion polypeptides are also encompassed by the present invention.

The plastid transit peptide is generally fused N-terminal to the polypeptide to be targeted (e.g., the fusion partner). In one embodiment, the fusion protein consists essentially of the peptide transit plastid and the polypeptide to be targeted. In another embodiment, the fusion protein comprises the peptide transit plastid and the polypeptide to be targeted. In such embodiments, the plastid transit peptide is preferably at the N-terminus of the fusion protein. However, additional amino acid residues may be N-terminal to the plastid transit peptide providing that the fusion protein is at least partially targeted to a plastid. In a specific embodiment, the plastid transit peptide is in the N-terminal half, N-terminal third, or N-terminal quarter of the fusion protein.

Most or all of the plastid transit peptide is generally cleaved from the fusion protein upon insertion into the plastid. The position of cleavage may vary slightly between plant species, at different plant developmental stages, as a result of specific intercellular conditions, or the particular combination of transit peptide/fusion partner used. In one embodiment, the plastid transit peptide cleavage is homogenous such that the cleavage site is identical in a population of fusion proteins. In another embodiment, the plastid transit peptide is not homogenous, such that the cleavage site varies by 1-10 amino acids in a population of fusion proteins.

The plastid transit peptide can be recombinantly fused to a second protein in one of several ways. For example, a restriction endonuclease recognition site can be introduced into the nucleotide sequence of the transit peptide at a position corresponding to its C-terminal end, and the same or a compatible site can be engineered into the nucleotide sequence of the protein to be targeted at its N-terminal end. Care must be taken in designing these sites to ensure that the coding sequences of the transit peptide and the second protein are kept "in frame" to allow the synthesis of the desired fusion protein. In some cases, it may be preferable to remove the initiator methionine codon of the second protein when the new restriction site is introduced. The introduction of restriction endonuclease recognition sites on both parent molecules and their subsequent joining through recombinant DNA techniques may result in the addition of one or more extra amino acids between the transit peptide and the second protein. This generally does not affect targeting activity as long as the transit peptide cleavage site remains accessible and the function of the second protein is not altered by the addition of these extra amino acids at its N-terminus. Alternatively, one skilled in the art can create a precise fusion between the transit peptide and the second protein (with or without its initiator methionine) using gene synthesis (Stemmer et al., Gene 164:49-53 (1995)) or similar methods.

In addition, the transit peptide fusion can intentionally include amino acids downstream of the cleavage site. The amino acids at the N-terminus of the mature protein can affect the ability of the transit peptide to target proteins to plastids and/or the efficiency of cleavage following protein import. This may be dependent on the protein to be targeted. See, e.g., Comai et al., J. Biol. Chem. 263(29):15104-9 (1988).

The fusion partner (e.g., the polypeptide to be targeted) may be any polypeptide for which plastid localization is desired. Fusion partners may be full-length proteins (e.g., as they occur in nature) or may be modified versions of such proteins (e.g., portions or fragments thereof, variants, or other non-naturally occurring versions of a protein). Fusion partners can be from any organism, including, but are not limited to, proteins from bacteria, algae, yeast, plants, animals, as well as synthetic proteins. For example, polypeptides that may be included in fusion proteins include, but are not limited to, Bt toxin proteins (see, e.g., U.S. Pat. Nos. 6,489,542; 5,281,530; 5,322,932; U.S. patent application Ser. No. 11/067,557 filed Feb. 25, 2005; and PCT publication WO 92/04453); 5-enolpyruvyl-3-phosphoshikimate synthase (EPSP synthase) (see. e.g., U.S. Pat. Nos. 4,971,908; 6,225,114); glyphosate N-acetyl transferase (GAT) (see, e.g., U.S. Patent Publication No. 2003/0083480), acetolactate synthase (ALS) (see, e.g., U.S. Pat. No. 5,013,659), enzymes that modify a physiological process that occurs in a plastid (e.g., photosynthesis or fatty acid, amino acid, oil, carotenoid, terpenoid, starch composition/synthesis) including, but not limited to, rubisco, rubisco activase, fatty acid synthase, fatty acid desaturase, phytoene synthase, phytoene desaturase, starch synthase, ADP-glucose pyrophosphorylase.

Different plastid transit peptides have differing degrees of efficacy (e.g., higher ratio of targeted to non-targeted fusion partner) when used in combination with different fusion partners. The particular plastid transit peptide to use in combination with a particular fusion partner can be determined empirically using, e.g., the assays described in section 4.4.

4.3 Nucleic Acid Molecules of the Invention

The present invention also relates to nucleic acid molecules that encode any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57, or any variants (e.g., any fragment, derivative, or analog) thereof.

In one embodiment, nucleic acid molecules encompassed by the present invention have plastid transit functional activity (e.g., the ability to direct an attached moiety into a plastid) and hybridize under stringent conditions to any one of the nucleic acid molecules that encode any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57.

In another embodiment, nucleic acid molecules encompassed by the present invention have plastid transit functional activity (e.g., the ability to direct an attached moiety into a plastid) and are a fragment comprising at least 70%, 75%, 85%, 90%, 95%, 97%, 98%, or 99% of the contiguous nucleic acid residues of any one of the nucleic acid molecules that encode any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57.

In another embodiment, nucleic acid molecules encompassed by the present invention have plastid transit functional activity (e.g., the ability to direct an attached moiety into a plastid) and comprise a nucleotide sequence that encodes a peptide that is at least 85%, 90%, 95%, 97%, 98%, or 99% identical to the amino acid sequence of any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57.

In another embodiment, nucleic acid molecules encompassed by the present invention have plastid transit functional activity (e.g., the ability to direct an attached moiety into a plastid) and comprise a nucleotide sequence which is at least 85%, 90%, 95%, 97%, 98%, or 99% identical to any of the nucleic acid molecules that encodes any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, and SEQ ID NO:57.

Vectors or expression cassettes comprising nucleic acid molecules of the invention are also encompassed (see Section 4.6). Cells, plants, or seeds comprising the vectors of the invention are also encompassed (see Section 4.7).

4.4 Methods to Assay for Plastid Transit Peptide Activity

Plastid transit peptide function or activity can be assayed by any method known in the art (see e.g., Lee et al., 2002, Mol. Cells. 14:388-97; Archer and Keegstra, 1993, Plant Mol. Biol. 23:1105-15; Reiss et al., 1989, Proc Natl Acad Sci USA. 86:886-90, Rensink et al., 1998, Plant Physiol. 118: 691-9; Kindle and Lawrence, 1998, Plant Physiol. 116:1179-90; Jin et al., 2003, Plant Mol. Biol. 51:493-507). As used herein, plastid transit peptide activity or function refers to the ability of a plastid transit peptide to direct an attached moiety (e.g., polypeptide) to a plastid. When attached to a functioning plastid transit peptide, the attached moiety is enriched (e.g., by at least 50%, 60%, 70%, 75%, 80%, 85%, 90%, 95%, 99%, or 100% as compared to a moiety not attached to the plastid transit peptide) in one or more plastids.

Typically, activity of a plastid transit peptide is compared to a positive (i.e., a transit peptide known to target the particular fusion partner) and/or a negative control (i.e., the polypeptide lacking a plastid transit peptide or comprising a non-functional plastid transit peptide). Assays for transit peptide activity may involve, but are not limited to, constructing recombinant fusions between a candidate plastid transit peptide and a fusion partner polypeptide and expressing the fusion in a plant or plant cell.

In one embodiment, the fusion polypeptide is functional only or substantially only in the plastid; thus, plastid localization of the fusion partner is determined by the functionality of the fusion partner. In a specific embodiment, the enzymatic activity (e.g., by making a colorimetric or other readily-detectable product) of the fusion partner is assayed. For example, lysine decarboxylase can be targeted to plastids and the accumulation of cadaverine monitored as an indication of enzyme targeting efficiency (see, e.g., Herminghaus et al., 1991, *Plant Mol. Biol.* 17:475-486 and Herminghaus et al., 1996, *Transgenic Research* 5:193-201). The conversion of L-trytophan to tryptamine by plastid-targeted trytophan decarboxylase can be measured as an indication of enzyme targeting efficiency (see, e.g., Fiore et al. 2002, *Plant Physiol.* 129:1160-1169). Changes in the distribution of existing carotenoid pigments, or the accumulation of non-native carotenoids can be examined as an indication of proper targeting and activity of various carotenoid biosynthetic enzymes (see, e.g., Kumagai et al., 1998, *Plant J* 14:305-315).

In another embodiment, the fusion polypeptide is fluorescent; thus, plastid localization of the fusion partner is determined by monitoring the accumulation of fluorescence in the plastids using, e.g., a fluorescence microscope. A preferred fluorescent protein is green fluorescent protein and variants thereof (see, e.g., Nakrieko et al., 2004, *Eur J Biochem.* 271:509-516; Belluci et al., 2003, *Plant Cell Rep.* 22:328-337; Chiu et al., 1996, *Curr Biol.* 6:325-330).

In another embodiment, plastid localization of the fusion partner is determined by determining the size of the fusion partner. Plastid transit peptides are typically cleaved in their entirety or in part when the fusion is inserted into a plastid. If the plastid transit peptide contains a cleavage site that is accessible as part of the fusion protein, then the plastid transit peptide will be cleaved off and the length (and therefore the molecular weight) of the polypeptide will be decreased. If the sequence of the cleavage site is not readily accessible, (e.g., if the surrounding sequences prevent proper recognition of the cleavage site or if the fusion protein folds in a way such that the stromal protease cannot gain access to the cleavage site) then cleavage will be inefficient and may occur at one or more alternative positions. Although the processed fusion partner polypeptides in this case will be of slightly varied length, they will still all be decreased in length and molecular weight from unprocessed polypeptide.

In another embodiment, plastids are isolated from plant tissue and then assayed for the presence of the fusion partner polypeptide. Any method known in the art for polypeptide detection can be used to assay for the presence of the fusion partner including, immunoblot, immunoprecipitation, ELISA, or detection of a trait of the fusion partner (e.g., fluorescence or enzymatic activity).

A transit peptide is deemed to be functional if the level of end-product production, fluorescent protein accumulation inside plastids, or mature protein accumulation in the above assays exceeds that of the negative control. A plastid transit peptide is considered to be efficient if the above parameters reach or exceed 50%, 60%, 70%, 75%, 80%, 85%, 90%, 95%, 99% of the level achieved by the positive control. In one embodiment, the plastid transit peptide used as a positive control is the transit peptide from the ribulose bisphosphate carboxylase-oxygenase small subunit gene (see for example, Comai et al., *J. Biol. Chem.* 263:15104-15109, 1988; Herminghaus et al., *Plant Mol. Biol.* 17:475-486, 1991).

4.5 Methods of Use

Plastid transit peptides can be used to target an attached moiety (e.g., polypeptide) to a plant plastid. In one embodiment, the plastid transit peptide directs localization to all plastids in all tissue types. In another embodiment, the plastid transit peptide directs localization to a subset of plastids in all tissue types. In another embodiment, the plastid transit peptide directs localization to all plastids in a subset of tissue types. In another embodiment, the plastid transit peptide directs localization to a subset of plastids in a subset of tissue types.

In one embodiment, the attached polypeptide targeted to a plastid is involved in a physiological process that takes place in the plastid (including, but not limited to, photosynthesis or fatty acid, amino acid, oil, carotenoid, terpenoid, starch composition/biosynthesis). As such, the targeted recombinant polypeptides can modulate or alter the physiological processes that occur in the plastids (e.g., by altering the levels of the enzyme and/or providing an altered enzyme with a function slightly different than the wild type enzyme). In a specific embodiment, the fusion partner is altered in a such a way to make the plant resistant to one or more herbicides. In a more specific embodiment, the fusion partner is acetolactate synthase (ALS) mutated to be resistant to one or more herbicides (see, e.g., U.S. Pat. No. 5,013,659).

In another embodiment, recombinant polypeptides are expressed and directed to plastids by the methods of the present invention to facilitate higher expression levels. For example, some polypeptides are toxic when expressed recombinantly in the cytoplasm of a plant cell and/or some polypeptides are sensitive to proteases and other constituents of the cytoplasm that case degradation. Because plastids are subcellular compartments, it is possible to target recombinant polypeptides to the plastids to sequester them from the cytoplasm, thus allowing for higher expression levels. In a specific embodiment, the fusion partner has insecticidal activity. In a more specific embodiment, the fusion partner is one or more Bt toxin proteins (see, e.g., U.S. Pat. Nos. 6,489,542; 5,281,530; 5,322,932; U.S. patent application Ser. No. 11/067,557 filed Feb. 25, 2005; and PCT publication WO 92/04453).

In another embodiment, recombinant polypeptides are expressed and directed to plastids by the methods of the present invention to avoid adverse agronomic effects to the plant. Some polypeptides are toxic or cause undesirable plant phenotypes when expressed recombinantly in the cytoplasm of a plant cell. By sequestering the recombinant polypeptides to the plastids, these unwanted effects can often be reduced or eliminated.

In another embodiment, recombinant polypeptides are expressed and directed to plastids by the methods of the present invention to facilitate easier isolation of the polypeptide. Plastids can be isolated from plant tissue by any method known in the art and the polypeptides contained in them extracted.

In another embodiment, recombinant polypeptides are expressed and directed to plastids by the methods of the present invention to facilitate higher expression levels. Some polypeptides are sensitive to proteases and other constituents of the cytoplasm. Because plastids are subcellular compartments, it is possible to target recombinant polypeptides to the plastids to sequester them from the cytoplasm, thus allowing for higher expression levels.

In another embodiment, recombinant polypeptides are expressed and directed to plastids by the methods of the present invention to regulate their activity on a substrate(s) that is localized in a different subcellular compartment. By separating the polypeptides/enzymes and substrate(s) into different subcellular compartments, the activity of the enzymes can be controlled by processes such as heating, grinding, or mechanical extraction that result in mixing of the enzymes and substrate(s) together.

In another embodiment, a recombinant polypeptide that forms a heteromeric complex is expressed and directed to plastids by the methods of the present invention to regulate the activity of the assembled enzyme complex. By separating components of the complex into different subcellular compartments, the activity of the assembled complex can be controlled by processes such as heating, grinding, or mechanical extraction that result in mixing of the polypeptide components together.

4.6 Recombinant Expression

Nucleic acid molecules and polypeptides of the invention can be expressed recombinantly using standard recombinant DNA and molecular cloning techniques that are well known in the art (e.g., Sambrook, Fritsch, and Maniatis, *Molecular Cloning: A Laboratory Manual*; Cold Spring Harbor Laboratory Press: Cold Spring Harbor, 1989). Additionally, recombinant DNA techniques may be used to create nucleic acid constructs suitable for use in making transgenic plants (see Section 4.7).

Accordingly, an aspect of the invention pertains to vectors, preferably expression vectors, comprising a nucleic acid molecule of the invention, or a variant thereof. As used herein, the term "vector" refers to a polynucleotide capable of transporting another nucleic acid to which it has been linked. One type of vector is a "plasmid", which refers to a circular double stranded DNA loop into which additional DNA segments can be introduced. Another type of vector is a viral vector, wherein additional DNA segments can be introduced into the viral genome.

Certain vectors are capable of autonomous replication in a host cell into which they are introduced (e.g., bacterial vectors having a bacterial origin of replication and episomal vectors). Other vectors (e.g., non-episomal vectors) are integrated into the genome of a host cell upon introduction into the host cell, and thereby are replicated along with the host genome. In general, expression vectors of utility in recombinant DNA techniques are often in the form of plasmids (vectors). However, the invention is intended to include such other forms of expression vectors, such as viral vectors (e.g., replication defective retroviruses).

The recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably associated with the polynucleotide to be expressed. Within a recombinant expression vector, "operably associated" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described in the art (e.g., Goeddel, *Gene Expression Technology: Methods in Enzymology,* 1990, Academic Press, San Diego, Calif.). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, the area of the organism in which expression is desired, etc. The expression vectors of the invention can be introduced into host cells to thereby produce proteins or peptides, including fusion proteins or peptides, encoded by nucleic acids molecules as described herein.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, U.S. Pat. No. 5,565,350; International Patent Application No. PCT/US93/03868), or isolated promoters can be introduced into a plant cell in the proper orientation and distance from a cognate gene of a polynucleotide of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making heterologous promoters and/or enhancers operably linked to a native, endogenous (i.e., non-heterologous) form of a polynucleotide of the present invention.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

The recombinant expression vectors of the invention can be designed for expression of a polypeptide of the invention in prokaryotic (e.g., *Enterobacteriaceae,* such as *Escherichia; Bacillaceae; Rhizoboceae,* such as *Rhizobium* and *Rhizobacter; Spirillaceae,* such as photobacterium; *Zymomonas; Serratia; Aeromonas; Vibrio; Desulfovibrio; Spirillum; Lactobacillaceae; Pseudomonadaceae,* such as *Pseudomonas* and *Acetobacter; Azotobacteraceae* and *Nitrobacteraceae*) or eukaryotic cells (e.g., insect cells using baculovirus expression vectors, yeast cells, plant cells, or mammalian cells) (see Goeddel, supra. For a discussion on suitable host cells). Alternatively, the recombinant expression vector can be transcribed and translated in vitro, for example using T7 promoter regulatory sequences and T7 polymerase.

Expression of proteins in prokaryotes is most often carried out in *E. coli* with vectors comprising constitutive or inducible promoters directing the expression of either fusion or non-fusion proteins. Fusion vectors add a number of amino acids to a protein encoded therein, usually to the amino terminus of the recombinant protein. Such fusion vectors typically serve at least three purposes: 1) to increase expression of the recombinant protein; 2) to increase the solubility of the recombinant protein; and/or 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corp., San Diego, Calif.), and pPicZ (Invitrogen Corp., San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell. Biol.* 3:2156-2165) and the pVL series (Lucklow and Summers, 1989, *Virology* 170:31-39).

In yet another embodiment, a nucleic acid of the invention is expressed in plant cells using a plant expression vector including, but not limited to, tobacco mosaic virus and potato virus expression vectors.

Other suitable expression systems for both prokaryotic and eukaryotic cells are known in the art (see, e.g., chapters 16 and 17 of Sambrook et al. 1990, *Molecular Cloning, A Laboratory Manual,* 2d Ed., Cold Spring Harbor Laboratory, Cold Spring Harbor, N.Y.).

A number of promoters can be used in the practice of the invention. The promoters can be selected based on the desired outcome. The nucleic acids can be combined with constitutive, tissue-specific, inducible, or other promoters for expression in the host organism.

A "tissue-specific promoter" may direct expression of nucleic acids of the present invention in a specific tissue, organ or cell type. Tissue-specific promoters can be inducible. Similarly, tissue-specific promoters may only promote transcription within a certain time frame or developmental stage within that tissue. Other tissue specific promoters may be active throughout the life cycle of a particular tissue. One of ordinary skill in the art will recognize that a tissue-specific promoter may drive expression of operably linked sequences in tissues other than the target tissue. Thus, as used herein, a tissue-specific promoter is one that drives expression preferentially in the target tissue or cell type, but may also lead to some expression in other tissues as well. A number of tissue-specific promoters can be used in the present invention. With the appropriate promoter, any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. For expression of a polynucleotide of the present invention in the aerial vegetative organs of a plant, photosynthetic organ-specific promoters, such as the RBCS promoter (Khoudi et al., Gene 197:343, 1997), can be used. Root-specific expression of polynucleotides of the present invention can be achieved under the control of a root-specific promoter, such as, for example, the promoter from the ANR1 gene (Zhang and Forde, *Science,* 279:407, 1998). Other exemplary promoters include the root-specific glutamine synthetase gene from soybean (Hirel et al., 1992, *Plant Molecular Biology* 20:207-218) and the root-specific control element in the GRP 1.8 gene of French bean (Keller et al., 1991, *The Plant Cell* 3:1051-1061).

A "constitutive promoter" is defined as a promoter which will direct expression of a gene in all tissues and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of ordinary skill in the art. Such genes include for example, ACT11 from *Arabidopsis* (Huang et al. 1996, *Plant Mol. Biol.* 33:125-139), Cat3 from *Arabidopsis* (Genbank Accession No. U43147, Zhong et al., 1996, *Mol. Gen. Genet.* 251:196-203), the gene encoding stearoyl-acyl carrier protein desaturase from *Brassica napus* (Genbank Accession No. X74782, Solocombe et al. 1994, *Plant Physiol.* 104:1167-1176), GPc1 from maize (GenBank Accession No. X15596, Martinez et al., 1989, *J. Mol. Biol.* 208:551-565), and Gpc2 from maize (GenBank Accession No. U45855, Manjunath et al., 1997, *Plant Mol. Biol.* 33:97-112). Any strong, constitutive promoter, such as the CaMV 35S promoter, can be used for the expression of polynucleotides of the present invention throughout the plant.

The term "inducible promoter" refers to a promoter that is under precise environmental or developmental control. Examples of environmental conditions that may effect transcription by inducible promoters include anaerobic conditions, elevated temperature, the presence of light, or spraying with chemicals/hormones.

Suitable constitutive promoters for use in a plant host cell include, for example, cauliflower mosaic virus (CaMV) 35S transcription initiation region, the full-length transcript promoter of mirabilis mosaic virus (Dey and Maiti, *Plant Mol. Biol.* 40:771-782, (1999)), the 1'- or 2'-promoter derived from T-DNA of *Agrobacterium tumafaciens*, the full-length transcript promoter from peanut chlorotic streak virus (Maiti and Shepherd, *Biochem. Biophys. Res. Comm.* 244:440-444 (1998)), the 34S promoter from figwort mosaic virus (Maiti et al., *Transgen. Res.* 6:143-156 (1997); Sanger et al., *Plant Mol. Biol.* 14:433-443 (1990)), and the full-length transcript promoter from strawberry vein banding virus (U.S. Patent Publication No. 2002/0182593) as well as other transcription initiation regions from various plant genes known to those of skill. Such genes include for example, ACT11 from *Arabidopsis* (Huang et al. *Plant Mol. Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Biol.* 208: 551-565 (1989)), Gpc2 from maize (GenBank No. U45855, Manjunath et al, *Plant Mol. Biol.* 33:97-112 (1997)), rice actin (McElroy et al., 1990, *Plant Cell* 2:163-171); ubiquitin (Christensen et al., 1989, *Plant Mol. Biol.* 12:619-632 and Christensen et al., 1992, *Plant Mol. Biol.* 18:675-689); pEMU (Last et al., 1991, *Theor. Appl. Genet.* 81:581-588).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Accordingly, the present invention provides a host cell having an expression vector comprising a nucleic acid of the invention, or a variant thereof. A host cell can be any prokaryotic (e.g., *E. coli, Bacillus thuringiensis*) or eukaryotic cell (e.g., insect cells, yeast or plant cells). The invention also provides a method for expressing a nucleic acid of the invention thus making the encoded polypeptide comprising the steps of i) culturing a cell comprising a nucleic acid molecule of the invention under conditions that allow production of the encoded polypeptide; and ii) isolating the expressed polypeptide.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid molecules into a host cell, including calcium phosphate or calcium chloride co-precipitation, DEAE-dextran-mediated transfection, lipofection, or electroporation. Suitable methods for transforming or transfecting host cells can be found in the art (e.g., Sambrook, et al. supra.).

4.7 Production of Transgenic Plants

Any method known in the art can be used for transforming a plant or plant cell with a nucleic acid molecule of the present invention. Nucleic acid molecules can be incorporated into plant DNA (e.g., genomic DNA or chloroplast DNA) or be maintained without insertion into the plant DNA (e.g., through the use of artificial chromosomes). Suitable methods of introducing nucleic acid molecules into plant cells include microinjection (Crossway et al., 1986, *Biotechniques* 4:320-334); electroporation (Riggs et al., 1986, *Proc. Natl. Acad. Sci.* 83:5602-5606; D'Halluin et al., 1992, *Plant Cell* 4:1495-1505); *Agrobacterium*-mediated transformation (U.S. Pat. Nos. 5,563,055 and 5,981,840, Osjoda et al., 1996, *Nature Biotechnology* 14:745-750; Horsch et al., 1984, *Science* 233:496-498, Fraley et al., 1983, *Proc. Natl. Acad. Sci.* 80:4803, and *Gene Transfer to Plants*, Potrykus, ed., Springer-Verlag, Berlin 1995); direct gene transfer (Paszkowski et al, 1984, *EMBO J.* 3:2717-2722); ballistic particle acceleration (U.S. Pat. Nos. 4,945,050; 5,879,918; 5,886,244; 5,932,782; Tomes et al., 1995, "Direct DNA Transfer into Intact Plant Cells via Microprojectile Bombardment, in *Plant Cell, Tissues, and Organ Culture: Fundamental Methods,* ed. Gamborg and Phillips, Springer-Verlag, Berlin; and McCabe et al., 1988, *Biotechnology* 6:923-926); virus-mediated transformation (U.S. Pat. Nos. 5,889,191, 5,889,190, 5,866,785, 5,589,367 and 5,316,931); pollen transformation (De Wet et al., 1985, in *The Experimental Manipulation of Ovule Tissues*, ed. Chapman et al., Longman, N.Y., pp. 197-209); Leo 1 transformation (U.S. patent application Ser. No. 09/435,054 now U.S. Pat. No. 6,825,397; International Publication No. WO 00/28058); whisker-mediated transformation (Kaeppler et al., 1990, *Plant Cell Reports* 9:415-418; Kaeppler et al., 1992, *Theor. Appl. Genet.* 84:560-566); and chloroplast transformation technology (Bogorad, 2000, *Trends in Biotechnology* 18: 257-263; Ramesh et al., 2004, *Methods Mol. Biol.* 274:301-7; Hou et al., 2003, *Transgenic Res.* 12:111-4; Kindle et al., 1991, *Proc. Natl. Acad. Sci.* 88:1721-5; Bateman and Purton, 2000, *Mol Gen Genet.* 263:404-10; Sidorov et al., 1999, *Plant J.* 19:209-216).

The choice of transformation protocols used for generating transgenic plants and plant cells can vary depending on the type of plant or plant cell, i.e., monocot or dicot, targeted for transformation. Examples of transformation protocols particularly suited for a particular plant type include those for: potato (Tu et al., 1998, *Plant Molecular Biology* 37:829-838; Chong et al., 2000, *Transgenic Research* 9:71-78); soybean (Christou et al., 1988, *Plant Physiol.* 87:671-674; McCabe et al., 1988, *BioTechnology* 6:923-926; Finer and McMullen, 1991, *In Vitro Cell Dev. Biol.* 27P:175-182; Singh et al., 1998, *Theor. Appl. Genet.* 96:319-324); maize (Klein et al., 1988, *Proc. Natl. Acad. Sci.* 85:4305-4309; Klein et al., 1988, *Biotechnology* 6:559-563; Klein et al., 1988, *Plant Physiol.* 91:440-444; Fromm et al., 1990, *Biotechnology* 8:833-839; Tomes et al., 1995, "Direct DNA Transfer into Intact Plant Cells via Microprojectile Bombardment," in *Plant Cell, Tissue, and Organ Culture: Fundamental Methods*, ed. Gamborg (Springer-Verlag, Berlin)); cereals (Hooykaas-Van Slogteren et al., 1984, *Nature* 311:763-764; U.S. Pat. No. 5,736,369).

In some embodiments, more than one construct is used for transformation in the generation of transgenic plants and plant cells. Multiple constructs may be included in cis or trans positions. In preferred embodiments, each construct has a promoter and other regulatory sequences.

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in the art (e.g., Evans et al., *Protoplasts Isolation and Culture, Handbook of Plant Cell Culture*, pp. 124-176, MacMillilan Publishing Company, New York, 1983; and Binding, Regeneration of Plants, Plant Protoplasts, pp. 21-73, CRC Press, Boca Raton, 1985). Regeneration can also be obtained from plant callus, explants, organs, or parts thereof. Such regeneration techniques are also described in the art (e.g., Klee et al. 1987, Ann. Rev. of Plant Phys. 38:467-486).

The nucleic acid molecules of the invention can be used to target a polypeptide to a plastid in essentially any plant. Thus, the invention has use over a broad range of plants, including species from the genera *Agrotis, Allium, Ananas, Anacardium, Apium, Arachis, Asparagus, Athamantha, Atropa, Avena, Bambusa, Beta, Brassica, Bromus, Browaalia, Camellia, Cannabis, Carica, Ceratonia. Cicer, Chenopodium, Chicorium, Citrus, Citrullus, Capsicum, Carthamus, Cocos, Coffea, Coix, Cucumis, Cucurbita, Cynodon, Dactylis, Datura, Daucus, Dianthus, Digitalis, Dioscorea, Elaeis, Eliusine, Euphorbia, Festuca, Ficus, Fragaria, Geranium, Glycine, Graminae, Gossypium, Helianthus, Heterocallis, Hevea, Hibiscus, Hordeum, Hyoscyamus, Ipomoea, Lactuca, Lathyrus, Lens, Lilium, Linum, Lolium, Lotus, Lupinus, Lycopersicon, Macadamia, Macrophylla, Malus, Mangifera, Manihot, Majorana, Medicago, Musa, Narcissus, Nemesia, Nicotiana, Onobrychis, Olea, Olyreae, Oryza, Panicum, Panicum, Panieum, Pannisetum, Pennisetum, Petunia, Pelargonium, Persea, Pharoideae, Phaseolus, Phleum, Picea, Poa, Pinus, Pistachia, Pisum, Populus, Pseudotsuga, Pyrus, Prunus, Pseutotsuga, Psidium, Quercus, Ranunculus, Raphanus, Ribes, Ricinus, Rhododendron, Rosa, Saccharum, Salpiglossis, Secale, Senecio, Setaria, Sequoia, Sinapis, Solanum, Sorghum, Stenotaphrum, Theobromus, Trigonella, Trifolium, Trigonella, Triticum, Tsuga, Tulipa, Vicia, Vitis, Vigna*, and *Zea.*

In specific embodiments, transgenic plants are maize, tomato, potato, rice, soybean, cotton plants, sunflower, alfalfa, lettuce, or tobacco.

Transgenic plants may be grown and pollinated with either the same transformed strain or different strains. Two or more generations of the plants may be grown to ensure that expression of the desired nucleic acid molecule, polypeptide and/or phenotypic characteristic is stably maintained and inherited. One of ordinary skill in the art will recognize that after the nucleic acid molecule of the present invention is stably incorporated in transgenic plants and confirmed to be operable, it can be introduced into other plants by sexual crossing. Any of a number of standard breeding techniques can be used, depending upon the species to be crossed.

4.8 Determination of Expression in Transgenic Plants

Any method known in the art can be used for determining the level of expression in a plant of a nucleic acid molecule of the invention or polypeptide encoded therefrom. For example, the expression level in a plant of a polypeptide encoded by a nucleic acid molecule of the invention can be determined by immunoassay, immunoblot, quantitative gel electrophoresis, etc.

Additionally, the expression level in a plant of a polypeptide encoded by a nucleic acid molecule of the invention can be determined by the degree to which the phenotype of the transgenic plant is altered. In a specific embodiment, enhanced polypeptide targeting to plastids is the phenotype to be assayed. Such phenotypes include, but are not limited to, a change in the amount or composition of fatty acids, amino acids, oils, terpenoids, or starch in seeds or other tissues, enhanced tolerance to an applied herbicide, greater resistance to a pest (e.g., insect and/or nematode), and/or increase in harvestable seed/grain yield and/or plant biomass.

Determinations can be made using whole plants, tissues thereof, plant cell culture, or plastids purified therefrom.

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, and/or defined in the appended claims, be interpreted as descriptive and illustrative of the present invention. Modifications and variations of the present invention are possible in light of the above teachings.

5. EXAMPLES

The following example is offered to illustrate, but not to limit the claimed invention.

5.1 Example 1

A library of non-naturally occurring peptide sequences was recombinantly fused to a lysine decarboxylase (LDC) gene from *E. coli* and transiently expressed in *Nicotiana tabacum* BY-2 suspension cells via *Agrobacterium*-mediated transformation (see generally Newman et al., *Plant Cell* 5:701-714, 1993). After 4 days the cells were rapidly freeze-thawed, re-hydrated in water +0.5% formic acid for at least one hour, dispersed with a 96-well replicator pin device, and then the supernatants were collected by spinning the mixtures through a Millipore MAHVN45 filter plate. Dilutions of the supernatants were analyzed for the presence of the end-product cadaverine using LC-Mass Spectroscopy (MS) as follows:

A triple quadrupole MS instrument (Quattro LC, Micromass) equipped with electrospray LC/MS interface was connected with an HPLC pump (Agilent 1050) delivering 40/60 of $H_2O$/MeOH w/0.1% formic acid at 0.3 ml/min constant flow rate. A flow injection method was used in analysis with Twin Pal auto injector (Leap Technology), injecting 5 μl of sample solution into the MS with a rate of one-half minute per injection. The Mass Spectrometer was operated at MRM mode for quantification of cadaverine (MS/MS transaction: 102.8>85.8) and D-lysine (MS/MS transaction: 146.8>83.6). Peak heights and areas were determined for transit peptide library clones and compared to positive (tobacco small subunit transit peptide) and negative (no transit peptide) controls. (For additional background information, see Henninghaus et al., *Plant Mol. Biol.* 17:475-486, 1991, and Herminghaus et al., *Transgenic Research* 5:193-201, 1996.)

Using the above-described assay, the peptide sequences depicted in Table 1 were found to efficiently target the lysine decarboxylase protein to plastids when fused to the N-terminus of this protein.

TABLE 1

Efficient plastid transit peptides identified with an LDC fusion partner

| Clone | SEQ ID NO | Sequence |
|---|---|---|
| sCTP-6H1 | 1 | MAATTLTSALPGAFSSSQRPSAPFNLQRSPRVLRRFNRKTGRQPRGLVRAAKAQ |
| sCTP-8B6 | 2 | MAATAVTSASLGAFSSSQRPGASSNSQRSPRLLRRFNRKTGRQPRGLVLAAKAQ |
| sCTP-1F7 | 3 | MAATAVSSVLPGAFSSSQRSSSPFNSQRSLIVLRRFNRKRRRQRRGRVLAAKAQ |
| sCTP-1H1 | 4 | MAATTVSSALLSAFSSSQSPSASFSLQTLPIVLRRFNRKTGRKPRGRVLAAKAQ |
| sCTP-2B4 | 5 | MAATTLTSASPSAFSSSQSSGAPSNLQRSLRLLRRFNRKTGRQRLGRIRAAKAQ |
| sCTP-2C7 | 6 | MASSALSSASPGAFSSSQRPSAPFNLKTSPIVLRRFNRNTGRQPRRRIRAAKAQ |
| sCTP-2E7 | 7 | MAASALSSASLSAFSSSQSSSAPSSSKTSLRVLRRFNRKRGRQPRGLIRAAKAQ |
| sCTP-2F2 | 8 | MAATAVTSASLGAFSSSQSPSAPSSSKKSLRVLRRFNRKTGRKPRGRVRAAKAQ |
| sCTP-2G8 | 9 | MASTAVSSASPGAFSSSQSSGAPSNLQRSPILLRRFNRKRGRKPLGRIRAAKAQ |
| sCTP-2G9 | 10 | MASTTLTSASPSAFSSSQRPSAPSNSQRSPRVLRRFNRKRGRKPLRRVLAAKAQ |
| sCTP-3B9 | 11 | MAATALTSVLPGAFSSSQSPSAPFSLQRSPIVLRRFNRNRGRQPRGRVRAAKAQ |
| sCTP-3C1 | 12 | MAASALTSASLGAFSSSQRPSAPSNLQTSPIVLRRFNRKTGLQPRRRVRAAKAQ |
| sCTP-3C12 | 13 | MAATALTSASPSAFSSSQRPGAPSSSKTSPRLLRRFNRNTRRQRRGLVRAAKAQ |
| sCTP-3E10 | 14 | MASTAVSSASLGAFSSSQSSGASSSSKTLPILLRRFNRKTRRQPLRLVRAAKAQ |
| sCTP-3E12 | 15 | MAASALTSASLGAFSSSQSPGAPSSSQTSLRVLRRFNRKTGPQRLRRVRAAKAQ |
| sCTP-3E7 | 16 | MASTALSSASPGAFSSSQRPSSPSSSKTSLRVLRRFNRKTGLQRRGLVRAAKAQ |
| sCTP-3E9 | 17 | MASSALSSASPGAFSSSQRPGSSSSSQTSPILLRRFNRKTGRQRLRRVRAAKAQ |
| sCTP-3F7 | 18 | MAASALTSALPGAFSSSQRPSAPSSSQRLPRLLRRFNRNTGRQRLRRIRAAKAQ |
| sCTP-4B7 | 19 | MASTAVTSVSPSAFSSSQRPGAPSSLQRSPRVLRRFNRKTGRQRLGLVLAAKAQ |
| sCTP-4D6 | 20 | MASTAVSSALPSAFSSSQRSSSPSSLQTLPRLLRRFNRKRGRQRRRRVRAAKAQ |
| sCTP-4E1 | 21 | MAASTVSSVSPSAFSSSQRPGAPFSSQRLPRVLRRFNRNTRRQRRGRVLAAKAQ |
| sCTP-4E7 | 22 | MASTALTSALLGAFSSSQRPGASSSLKRSPRVLRRFNRNRRLKRLGRVRAAKAQ |
| sCTP-4F1 | 23 | MASTTVSSASPGAFSSSQRSSSPSNSQTSPRVLRRFNRKTGRKPRGLVRAAKAQ |
| sCTP-4F12 | 24 | MAATAVTSALPGAFSSSQRPSAPFNSKTSPIVLRRFNRKTGRQPRRRVRAAKAQ |
| sCTP-5D1 | 25 | MAASTLSSVSPGAFSSSQSPGAPSSSQRSPRVLRRFNRNTGLQPRGRIRAAKAQ |
| sCTP-5E1 | 26 | MASSALTSASPGAFSSSQRPSAPFNSQRSPILLRRFNRNTRRQRRGLIRAAKAQ |

TABLE 1-continued

| Efficient plastid transit peptides identified with an LDC fusion partner | | |
|---|---|---|
| Clone | SEQ ID NO | Sequence |
| sCTP-5G1 | 27 | MAASALTSVSLSAFSSSQRPGAPSSLKTSPRLLRRFNRNTGLQRRGRVRA AKAQ |
| sCTP-5H1 | 28 | MASTAVSSALLSAFSSSQSSGSPFSSQTLLRLLRRFNRNTGRQPLRRVLA AKAQ |
| sCTP-5H10 | 29 | MAATALTSASLGAFSSSQRSGSPSNSQTLPIVLRRFNRKTRLKPRGRVLA AKAQ |
| sCTP-5H2 | 30 | MASSAVTSALPGAFSSSQSPSAPSSSKRLPIVLRRFNRKTGRKPRGLVRA AKAQ |
| sCTP-5H5 | 31 | MAASALTSVSPGAFSSSQSPGAPSNSQTSLRVLRRFNRNTRRKPRGLVRA AKAQ |
| sCTP-5H6 | 32 | MAATALTSASLGAFSSSQRPGSSSNSQTSPILLRRFNRKTRLQRRRRVRA AKAQ |
| sCTP-6B1 | 33 | MAATTVTSASLGAFSSSQSPSAPFNSQTSPRVLRRFNRKTGRQPRGRVRA AKAQ |
| sCTP-6F1 | 34 | MASSTLTSALPGAFSSSQSSSASSSSQTSLRVLRRFNRKTGLKRLGRVRA AKAQ |
| sCTP-6G2 | 35 | MAASALTSASLSAFSSSQSSGASSSSQRSLRVLRRFNRKTGRQRRRRVLA AKAQ |
| sCTP-7D6 | 36 | MASTTVSSASPGAFSSSQRPGASSSLQRSPRVLRRFNRNRGRQRRGRVLA AKAQ |
| sCTP-7H1 | 37 | MASTTLSSASPGAFSSSQSPSAPFSSQRSLRVLRRFNRKRGRQPRGLVRA AKAQ |
| sCTP-8H1 | 38 | MASTTLSSASLGAFSSSQSPSAPFSSQRLLRVLRRFNRKRGRKPRGRVRA AKAQ |
| sCTP-5G11 | 39 | MASTTLSSASLASVSLGAFSSSQSPSAPSSSQTSPIVLRRFNRNTGRQPRRL VRAAKAQ |

5.2 Example 2

A library of non-naturally occurring peptide sequences was recombinantly fused to a Cry2 Bt toxin and transiently expressed in *Nicotiana benthamiana* leaves via *Agrobacterium*-mediated transformation (see Kapila et al., *Plant Science* 122:101-108, 1997). Protein was extracted from the infiltrated leaf tissue and analyzed by SDS-PAGE and western blotting. Since processing of proteins targeted to a plastid involves cleavage of the transit peptide sequence from the remainder of the protein, a decrease in molecular weight of the Cry2 protein relative to the initial transit peptide-Cry2 fusion is an indication that the peptide sequence mediated proper targeting to plastids and subsequent cleavage upon import. Using the above-described assay, the peptide sequences depicted in Table 2 were found to efficiently target the Cry2 protein to plastids when fused to the N-terminus of this protein.

TABLE 2

| Efficient plastid transit peptides identified with a Cry2 fusion partner | | |
|---|---|---|
| Clone | SEQ ID NO | Sequence |
| sCTP-6H1 | 1 | MAATTLTSALPGAFSSSQRPSAPFNLQRSPRVLRRFNRKTGRQPRGLVRA AKAQ |
| sCTP-20 | 40 | MAASTLSSASPSAFSSSQRPSAPSSLKTSLIVLRRFNRKTGRQPRGLVLAA KAQ |
| sCTP-A1 | 41 | MAASTLSSVSPGAFSSSQRSGAPSNLQRSPILLRRFNRKTGRQPRGRVRA AKAQ |
| sCTP-28 | 42 | MAATTVSSALPGAFSSSQSSGSSFNSKTLPRVLRRFNRNTGRQPLGLVRA AKAQ |

TABLE 2-continued

| Efficient plastid transit peptides identified with a Cry2 fusion partner | | |
|---|---|---|
| Clone | SEQ ID NO | Sequence |
| sCTP-27 | 43 | MASTAVTSALPGAFSSSQSPSAPSSLQTSPILLRRFNRNRGLKRLGRIRAA KAQ |
| sCTP-F1 | 44 | MASSALTSASPSAFSSSQSSSAPFNSQTSPIVLRRFNRNTGRQRRGRVLAA KAQ |
| sCTP-G4 | 45 | MASSAVTSASPSAFSSSQSPSAPFNSKRSPILLRRFNRKTGLQPRRLVRAA KAQ |
| sCTP-17 | 46 | MAATALTSALPGAFSSSQSPGAPSNLQTSPIVLRRFNRNTGRKPRGRILAA KAQ |
| sCTP-5 | 47 | MAATTLSSALPGAFSSSQSSSAPSNSQTSPILLRRFNRKTGLQPRRRVLAA KAQ |
| sCTP-11 | 48 | MAATALSSASLGAFSSSQRPGASSSLQRSLIVLRRFNRKTGRQRRGRVLA AKAQ |
| sCTP-12 | 49 | MASSAVTSASLSAFSSSQRPSASFNLQTSPRVLRRFNRKTGRQRLGLVRA AKAQ |
| sCTP-19 | 50 | MAATALTSALLGAFSSSQSPGASSSLQTSLIVLRRFNRNRGRQPRGRILAA KAQ |
| sCTP-21 | 51 | MAASTLSSVSPGAFSSSQSPGAPSSSQRSPRVLRRFNRNTGLQPRGRIRAA KAQ |
| sCTP-30 | 52 | MAASAVSPGAFSSSQSPGASSNSQRLLRVLRRFNRKTGLQPLGRIRAAKA Q |
| sCTP-G1 | 53 | MAATALSSASPGAFSSSQRPSAPSNSQTLPRVLRRFNRNTRRQPRGLVLA AKAQ |
| sCTP-A2 | 54 | MAATAVSSASPGAFSSSQRSSAPSSSQRLPIVLRRFNRKRGRQRRGLVLA AKAQ |
| SCTP-G2 | 55 | MAASALTSVLPGAFSSSQRPSAPSNSKRLPRLLRRFNRNTGLQPRGRILA AKAQ |
| sCTP-D3 | 56 | MASSALSSASLGAFSSSQSPSASFSSQTSPRLLRRFNRKTGLKRLGRVRA AKAQ |

5.3 Example 3

A small subset of the synthetic plastid transit peptides listed in Table 1 was tested for efficacy with a glyphosate acetyl transferase protein (see *Science* 304:1151-1154, 2004) using the *Nicotiana benthamiana* leaf infiltration assay described in Example 2. Using this assay, plastid transit peptides sCTP-6H1 and sCTP-6F1 were found to target the GAT protein to plastids with reasonable efficiency when fused to the N-terminus of this protein (data not shown).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated peptide comprising SEQ ID NO:1.

2. A fusion polypeptide comprising the peptide of claim 1.

3. An isolated peptide comprising an amino acid sequence that has at least 95% sequence identity to the amino acid sequence of SEQ ID NO: 1, and wherein the Deptide taraets a translationally fused polypeptide into plant plastids.

4. A fusion polypeptide comprising the peptide of claim 3.

5. An isolated peptide comprising an amino acid sequence that is encoded by a nucleic acid molecule, wherein the nucleic acid molecule comprises a nucleic acid sequence that has at least 95% sequence identity to the nucleic acid sequence that encodes SEQ ID NO:1, and wherein the peptide targets a translationally fused rolyreptide into plant plastids.

6. A fusion polypeptide comprising the peptide of claim 5.

7. An isolated peptide comprising an amino acid sequence that is encoded by a nucleic acid molecule, wherein the nucleic acid molecule hybridizes to a nucleic acid molecule that encodes SEQ ID NO: 1, wherein hybridization conditions comprise two washes in 0.2×SSC at 65° C. for 20 minutes each, and wherein the peptide targets a translationally fused polypeptide into plant plastids.

8. A fusion polypeptide comprising the peptide of claim 7.

9. An isolated peptide comprising an amino acid sequence having at least 90% sequence identity to SEQ ID NO: 1, and wherein the peptide targets a translationally fused polypeptide into plant plastids.

10. A fusion polypeptide comprising the peptide of claim 9.

* * * * *

UNITED STATES PATENT AND TRADEMARK OFFICE

CERTIFICATE OF CORRECTION

PATENT NO. : 7,345,143 B2
APPLICATION NO. : 11/619318
DATED : March 18, 2008
INVENTOR(S) : Michael Lassner et al.

It is certified that error appears in the above-identified patent and that said Letters Patent is hereby corrected as shown below:

In the Claims:

In Claim 3, line 3 (Col. 61, line 18) substitute "Deptide taraets" with --peptide targets--.

In Claim 5, line 6 (Col. 61, line 26) substitute "rolyreptide" with --polypeptide--.

In Claim 7, line 5 (Col. 62, line 17) substitute "0.2xSSC at 65° C. for" with --0.2x SSC at 65 °C for--.

Signed and Sealed this

Eighth Day of July, 2008

JON W. DUDAS

*Director of the United States Patent and Trademark Office*